(12) United States Patent
Miller

(10) Patent No.: US 8,343,073 B2
(45) Date of Patent: Jan. 1, 2013

(54) BIOPSY NEEDLE

(76) Inventor: Stuart H. Miller, Clifton, NJ (US)

( * ) Notice: Subject to any disclaimer, the term of this patent is extended or adjusted under 35 U.S.C. 154(b) by 225 days.

(21) Appl. No.: 12/585,266

(22) Filed: Sep. 10, 2009

(65) Prior Publication Data

US 2010/0076342 A1  Mar. 25, 2010

Related U.S. Application Data

(63) Continuation-in-part of application No. 11/228,466, filed on Sep. 19, 2005.

(60) Provisional application No. 60/610,542, filed on Sep. 17, 2004.

(51) Int. Cl.
*A61B 10/00* (2006.01)
(52) U.S. Cl. ........................................... 600/567
(58) Field of Classification Search .................. 600/567, 600/564, 566; 606/167
See application file for complete search history.

(56) References Cited

U.S. PATENT DOCUMENTS

| 5,320,110 A | * | 6/1994 | Wang | 600/566 |
| 5,458,112 A | * | 10/1995 | Weaver | 600/566 |
| 5,536,266 A | * | 7/1996 | Young et al. | 606/27 |
| 2002/0055404 A1 | * | 5/2002 | Liechty, II | 473/583 |

FOREIGN PATENT DOCUMENTS

WO  WO 94/08512  *  4/1994  .................... 600/567

* cited by examiner

*Primary Examiner* — Jeffrey G Hoekstra
*Assistant Examiner* — Fangemonique Smith
(74) *Attorney, Agent, or Firm* — Welsh Flaxman & Gitler LLC

(57) ABSTRACT

A biopsy needle includes an outer cannula and an inner cannula. The inner cannula includes a distal end and a proximal end, the outer cannula being shaped and dimensioned to closely circumscribe the inner cannula for movement relative thereto. The inner cannula further includes a sample recess at its distal end, the sample recess including a dual cavity recess, wherein a first cavity has a parabolic shape and the second cavity has a circular shape.

1 Claim, 37 Drawing Sheets

Biopsy Needle Design 2
****************************

From Figure 4 for a 20 Ga needle $ro := 0.0175 \quad h := 0.20 \quad \alpha := 10 \quad \gamma := 0$ $qn := ro \cdot (1 - \sin(\gamma \cdot deg)) \qquad ri := ro \cdot \sin(\gamma \cdot deg)$ $qn = 0.0175$ $xn := \dfrac{ro \cdot (1 - \sin(\gamma \cdot deg))}{\sin(\alpha \cdot deg)}$ $xn = 0.10078$ $pn := \dfrac{ro \cdot (1 - \sin(\gamma \cdot deg))}{\tan(\alpha \cdot deg)}$ $pn = 0.099247$ $in := ro \cdot \cos(\gamma \cdot deg)$ $in := 0.0175$ Plot graphs
*************

$qn(\gamma) := ro \cdot (1 - \sin(\gamma \cdot deg)) \qquad in(\gamma) := ro \cdot \cos(\gamma \cdot deg)$ $xn(\gamma) := \dfrac{ro \cdot (1 - \sin(\gamma \cdot deg))}{\sin(\alpha \cdot deg)} \qquad ri(\gamma) := ro \cdot \sin(\gamma \cdot deg)$ $pn(\gamma) := \dfrac{ro \cdot (1 - \sin(\gamma \cdot deg))}{\tan(\alpha \cdot deg)}$ $in(60) = 8.75 \times 10^{-3}$ $qn(60) = 2.344555 \times 10^{-3} \qquad xn(60) = 0.013502 \qquad pn(60) = 0.013297$ $ri(60) = 0.015155$

FIG. 8

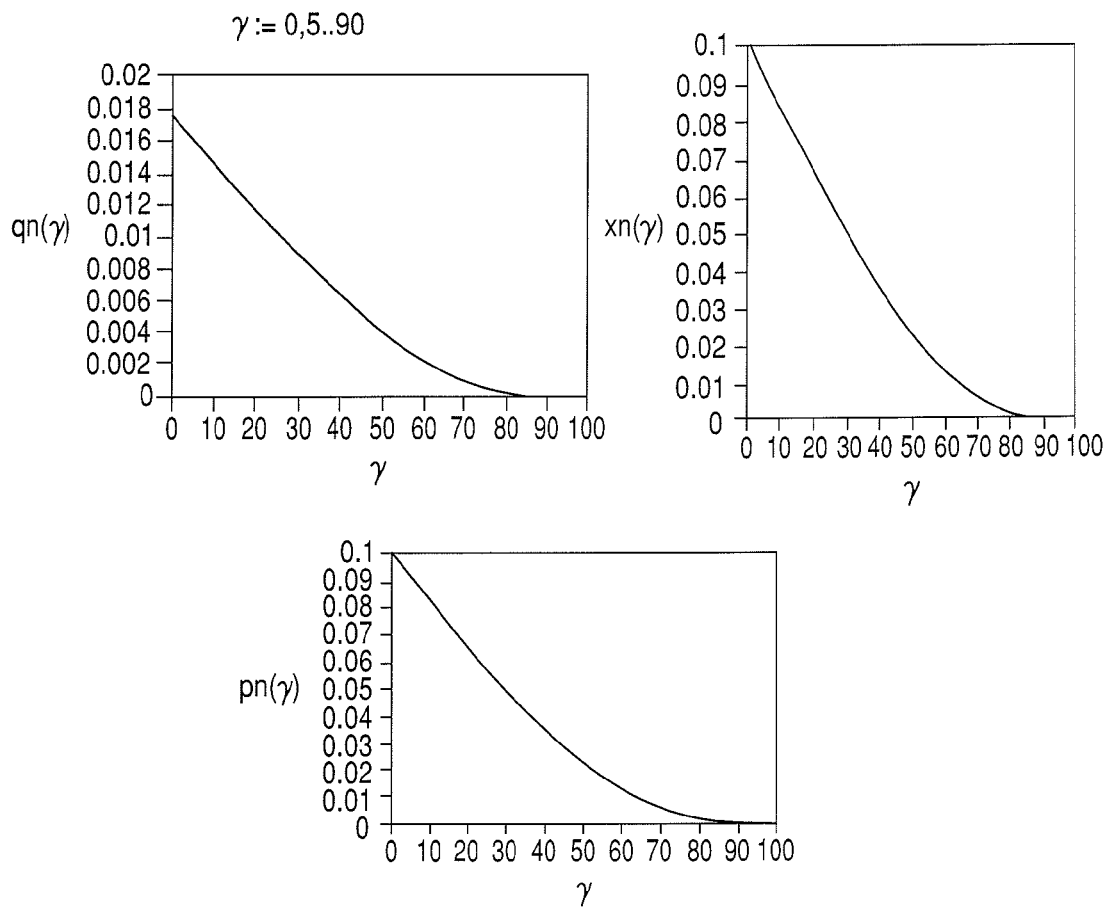
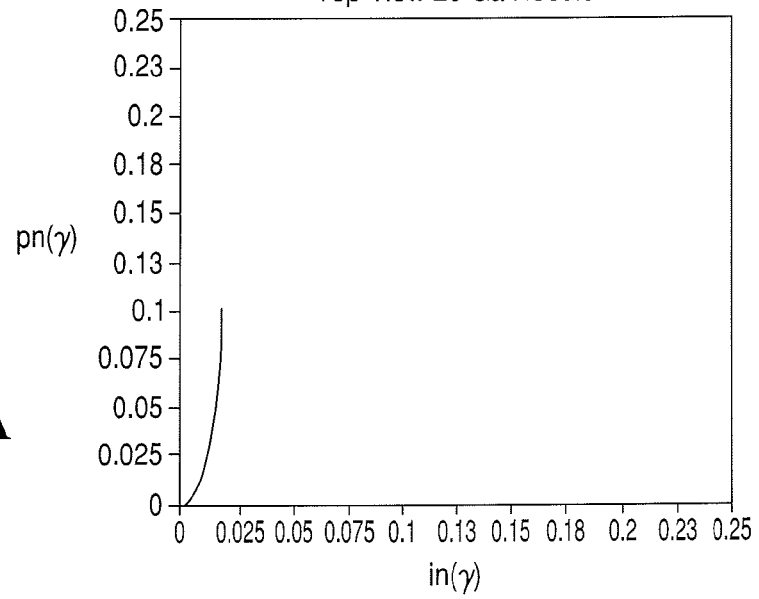
FIG. 8A

For a 14 Ga needle
*********************

$ro := 0.0415 \quad h := 0.20 \quad \alpha := 10 \quad \gamma := 0$ $qn := ro \cdot (1 - \sin(\gamma \cdot deg)) \qquad ri := ro \cdot \sin(\gamma \cdot deg)$ $qn = 0.0415$ $xn := \dfrac{ro \cdot (1 - \sin(\gamma \cdot deg))}{\sin(\alpha \cdot deg)}$ $xn = 0.238989$ $pn := \dfrac{ro \cdot (1 - \sin(\gamma \cdot deg))}{\tan(\alpha \cdot deg)}$ $pn = 0.235358$ $in := ro \cdot \cos(\gamma \cdot deg)$ $in := 0.0415$ Plot graphs
************

$qn(\gamma) := ro \cdot (1 - \sin(\gamma \cdot deg)) \qquad in(\gamma) := ro \cdot \cos(\gamma \cdot deg)$ $ri(\gamma) := ro \cdot \sin(\gamma \cdot deg)$ $xn(\gamma) := \dfrac{ro \cdot (1 - \sin(\gamma \cdot deg))}{\sin(\alpha \cdot deg)}$ $pn(\gamma) := \dfrac{ro \cdot (1 - \sin(\gamma \cdot deg))}{\tan(\alpha \cdot deg)}$ $qn(0) = 0.0415 \qquad xn(0) = 0.238989 \qquad pn(0) = .0235358 \qquad in(0) = 0.0415$ $ri(0) = 0$

FIG. 9

For the 14 Ga needle example above
*******************************************
$\gamma := 0, 5 .. 90$
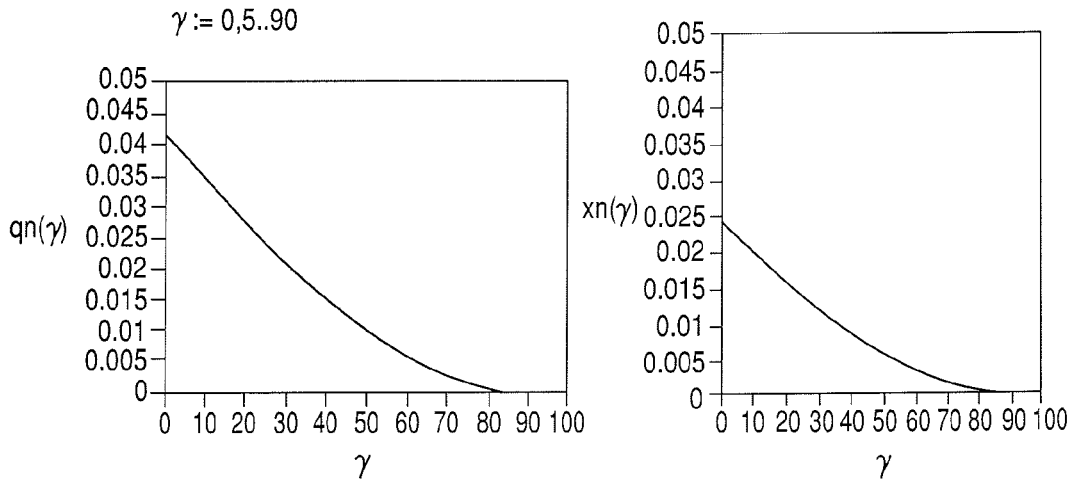
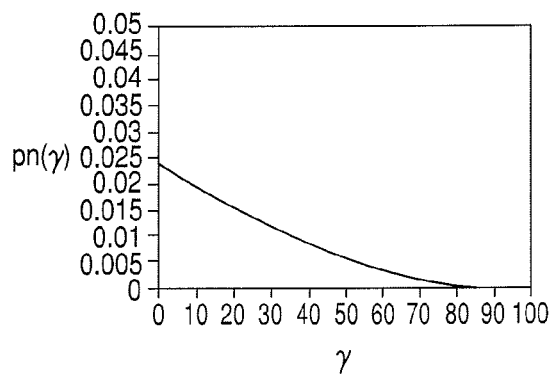
Top View 14 Ga Needle
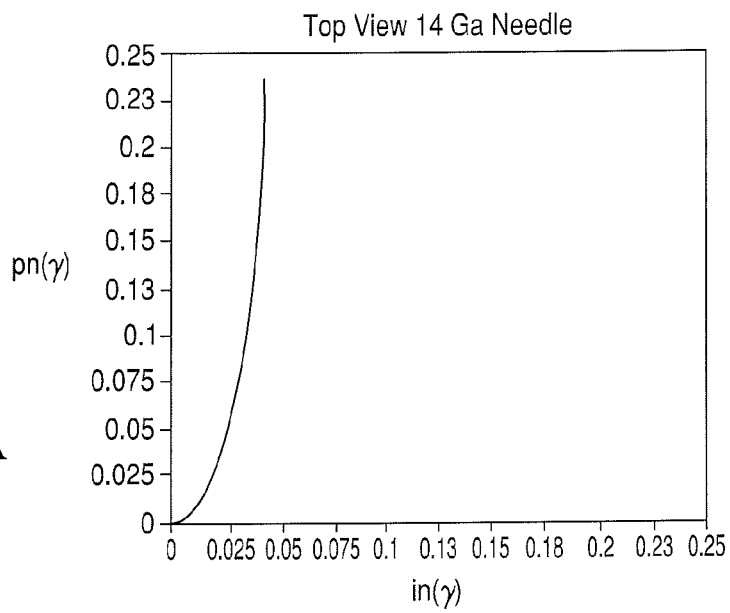
FIG. 9A For a 18 Ga needle
*********************

$ro := 0.0245 \quad h := 0.20 \quad \alpha := 10 \quad \gamma := 0$ $qn := ro \cdot (1 - \sin(\gamma \cdot deg)) \qquad ri := ro \cdot \sin(\gamma \cdot deg)$ $qn = 0.0245$ $xn := \dfrac{ro \cdot (1 - \sin(\gamma \cdot deg))}{\sin(\alpha \cdot deg)}$ $xn = 0.14109$ $pn := \dfrac{ro \cdot (1 - \sin(\gamma \cdot deg))}{\tan(\alpha \cdot deg)}$ $pn = 0.138946$ $in := ro \cdot \cos(\gamma \cdot deg)$ $in := 0.0245$ Plot graphs
************

$qn(\gamma) := ro \cdot (1 - \sin(\gamma \cdot deg)) \qquad in(\gamma) := ro \cdot \cos(\gamma \cdot deg)$ $ri(\gamma) := ro \cdot \sin(\gamma \cdot deg)$ $xn(\gamma) := \dfrac{ro \cdot (1 - \sin(\gamma \cdot deg))}{\sin(\alpha \cdot deg)}$ $pn(\gamma) := \dfrac{ro \cdot (1 - \sin(\gamma \cdot deg))}{\tan(\alpha \cdot deg)}$ $qn(0) = 0.0245 \quad xn(0) = 0.14109 \quad pn(0) = .138946 \quad in(0) = 0.0245$ $ri(0) = 0$

FIG. 10

Plot the equations for $\gamma = -90$ to $\gamma = +90$ degrees & $\alpha = 10$ degrees
*********************************************************************

From Figure 4 for a 20 Ga needle $ro := 0.0175 \qquad h := 0.20 \qquad \alpha := 10 \qquad \gamma := -90, -88 .. 90$ $qn(\gamma) := ro \cdot (1 - \sin(\gamma \cdot deg)) \qquad in(\gamma) := ro \cdot \cos(\gamma \cdot deg)$ $ri(\gamma) := ro \cdot \sin(\gamma \cdot deg)$ $xn(\gamma) := \dfrac{ro \cdot (1 - \sin(\gamma \cdot deg))}{\sin(\alpha \cdot deg)}$ $pn(\gamma) := \dfrac{ro \cdot (1 - \sin(\gamma \cdot deg))}{\tan(\alpha \cdot deg)}$ $qn(0) = 0.0175 \qquad xn(0) = 0.100778 \qquad pn(0) = 0.099247 \qquad in(0) = 0.0175$ $ri(0) = 0$ For the 20 Ga needle and a grind angle $\alpha = 10$ degrees the graph below shows the geometry parameters for the selected biopsy cavity. The biopsy needle centerline is at $\gamma = 0$ deg. For positive values of the angle $\gamma$, the bottom of the biopsy cavity is above the biopsy needle centerline. For negative values of the angle $\gamma$, the bottom of the biopsy cavity is below the biopsy needle centerline and testing should be undertaken to preclude fracture of the needle tip.

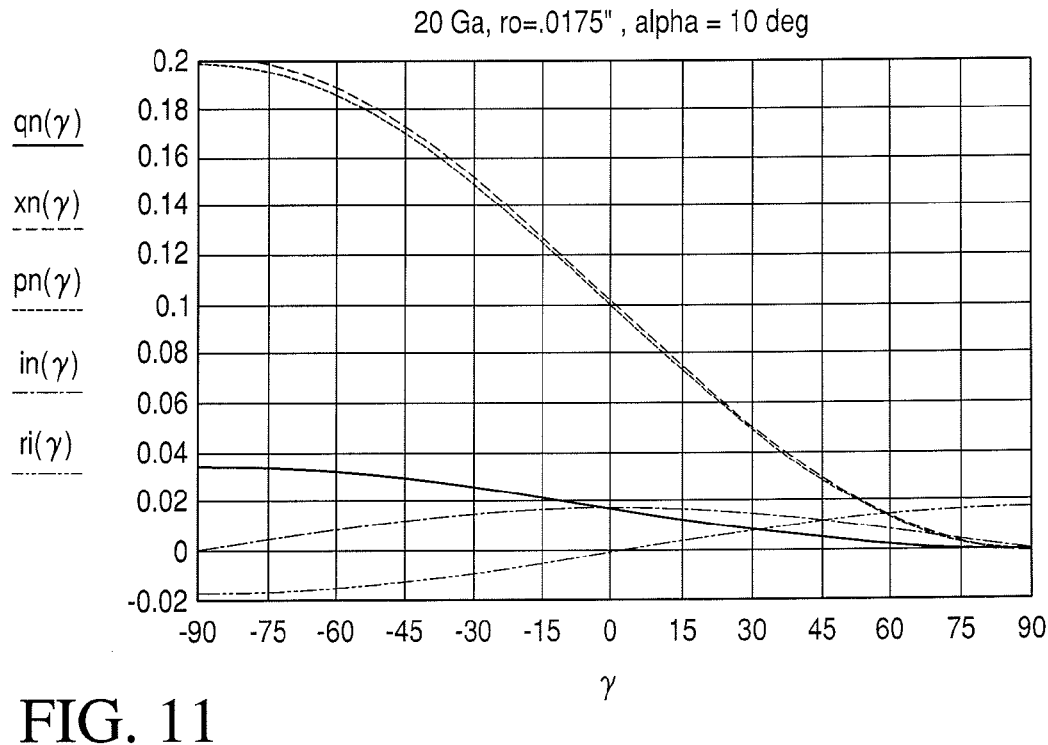

FIG. 11

For a 14 Ga needle
********************** ro := 0.0415     h := 0.20     α := 10     γ := -90,-88..90

Plot graphs
*************

$qn(\gamma) := ro \cdot (1 - \sin(\gamma \cdot deg))$     $in(\gamma) := ro \cdot \cos(\gamma \cdot deg)$ $xn(\gamma) := \dfrac{ro \cdot (1 - \sin(\gamma \cdot deg))}{\sin(\alpha \cdot deg)}$     $ri(\gamma) := ro \cdot \sin(\gamma \cdot deg)$ $pn(\gamma) := \dfrac{ro \cdot (1 - \sin(\gamma \cdot deg))}{\tan(\alpha \cdot deg)}$ qn(0) = 0.0415    xn(0) = 0.238989    pn(0) = 0.235358    in(0) = 0.0415 ri(0) = 0

For a 18 Ga needle
********************* ro := 0.0245    h := 0.20    α := 10    γ := -90,-88..90

Plot graphs
*************

$qn(\gamma) := ro \cdot (1 - \sin(\gamma \cdot deg))$ $in(\gamma) := ro \cdot \cos(\gamma \cdot deg)$ $xn(\gamma) := \dfrac{ro \cdot (1 - \sin(\gamma \cdot deg))}{\sin(\alpha \cdot deg)}$ $ri(\gamma) := ro \cdot \sin(\gamma \cdot deg)$ $pn(\gamma) := \dfrac{ro \cdot (1 - \sin(\gamma \cdot deg))}{\tan(\alpha \cdot deg)}$ qn(0) = 0.0245    xn(0) = 0.14109    pn(0) = 0.138946    in(0) = 0.0245 ri(0) = 0

For comparison purposes, let's change the angle of the cutting edge of the biopsy needle, α, from 10 degrees to 20 degrees
*******************************************************************************

For the 20 Ga needle, we have the following:

ro := 0.0175    h := 0.20    α := 20    γ := -90,-88..90

$qn(\gamma) := ro \cdot (1 - \sin(\gamma \cdot deg))$    $in(\gamma) := ro \cdot \cos(\gamma \cdot deg)$ $xn(\gamma) := \dfrac{ro \cdot (1 - \sin(\gamma \cdot deg))}{\sin(\alpha \cdot deg)}$    $ri(\gamma) := ro \cdot \sin(\gamma \cdot deg)$ $pn(\gamma) := \dfrac{ro \cdot (1 - \sin(\gamma \cdot deg))}{\tan(\alpha \cdot deg)}$ $in(\gamma) := ro \cdot \cos(\gamma \cdot deg)$ qn(0) = 0.0175    xn(0) = 0.051167    pn(0) = 0.048081    in(0) = 0.0175 ri(0) = 0

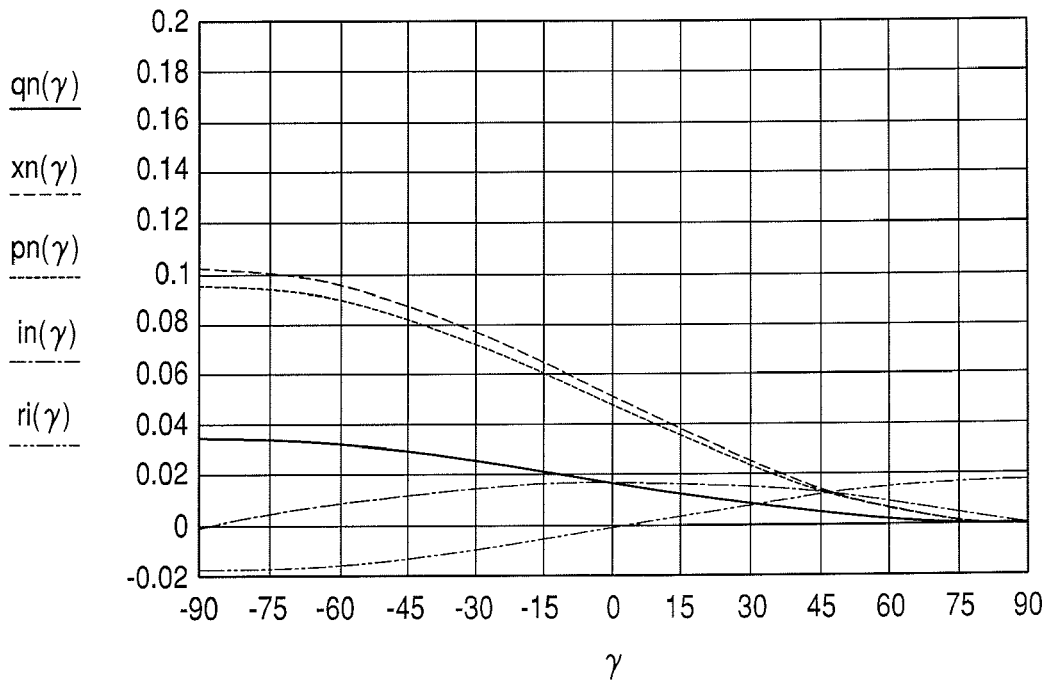

FIG. 14

For a 14 Ga needle
********************* ro := 0.0415    h := 0.20    α := 20    γ := −90,−88..90

Plot graphs $qn(\gamma) := ro \cdot (1 - \sin(\gamma \cdot \deg))$     $in(\gamma) := ro \cdot \cos(\gamma \cdot \deg)$ $xn(\gamma) := \dfrac{ro \cdot (1 - \sin(\gamma \cdot \deg))}{\sin(\alpha \cdot \deg)}$     $ri(\gamma) := ro \cdot \sin(\gamma \cdot \deg)$ $pn(\gamma) := \dfrac{ro \cdot (1 - \sin(\gamma \cdot \deg))}{\tan(\alpha \cdot \deg)}$ qn(0) = 0.0415    xn(0) = 0.121338    pn(0) = 0.11402    in(0) = 0.0415 ri(0) = 0

For a 18 Ga needle
********************* ro := 0.0245     h := 0.20     α := 20     γ := -90,-88..90

Plot graphs
*************

$qn(\gamma) := ro \cdot (1 - \sin(\gamma \cdot deg))$     $in(\gamma) := ro \cdot \cos(\gamma \cdot deg)$ $xn(\gamma) := \dfrac{ro \cdot (1 - \sin(\gamma \cdot deg))}{\sin(\alpha \cdot deg)}$     $ri(\gamma) := ro \cdot \sin(\gamma \cdot deg)$ $pn(\gamma) := \dfrac{ro \cdot (1 - \sin(\gamma \cdot deg))}{\tan(\alpha \cdot deg)}$ qn(0) = 0.0245     xn(0) = 0.071633     pn(0) = 0.067313     in(0) = 0.0245 ri(0) = 0

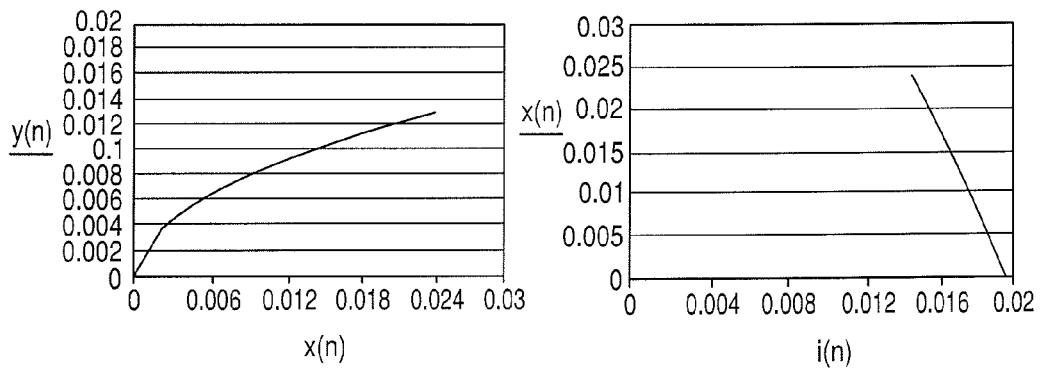
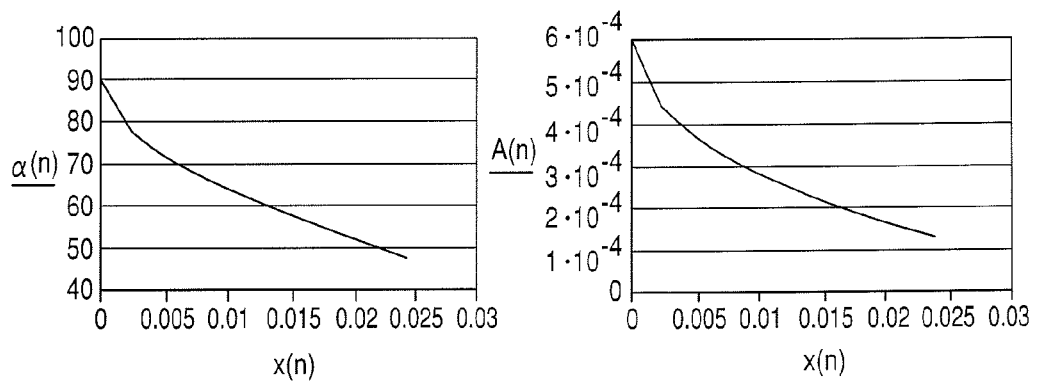
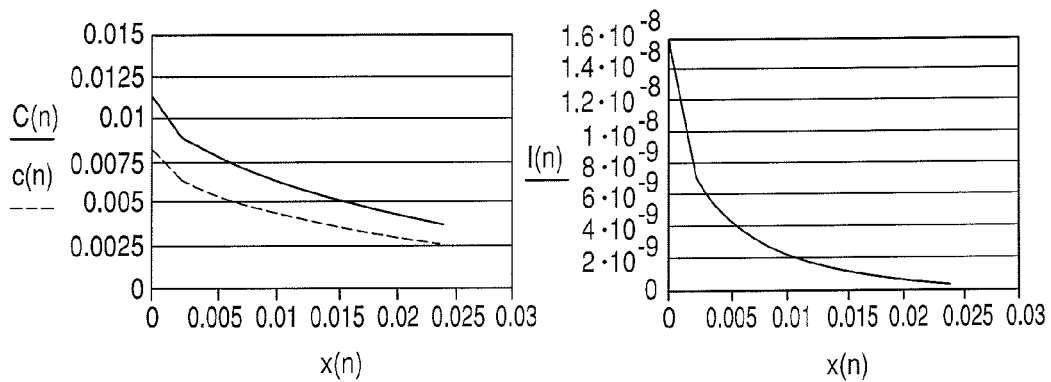
FIG. 22

Dual Cavity Geometry
*************************

$$x := \begin{pmatrix} 0 \\ .0005 \\ .0006 \\ .0007 \\ .0008 \\ .0009 \\ .001 \\ .00125 \\ .0015 \\ .00175 \\ .002 \\ .00225 \\ .0024 \\ .0048 \\ .0072 \\ .0096 \\ .012 \\ .0144 \\ .0168 \\ .0192 \\ .0216 \\ .024 \\ .025612 \\ .027258 \\ .028936 \\ .030642 \\ .032375 \\ .034132 \\ .035911 \\ .037709 \\ .038796 \\ .0391602 \\ .039525 \\ .039889 \\ .040255 \\ .040621 \\ .040987 \\ .041354192 \end{pmatrix} \quad y := \begin{pmatrix} 0 \\ .00187639 \\ .00205548 \\ .00222017 \\ .00237346 \\ .00251744 \\ .00265361 \\ .00296683 \\ .00325 \\ .003510401 \\ .00375277 \\ .0039804 \\ .004110961 \\ .005813777 \\ .007120393 \\ .008221922 \\ .009192388 \\ .01007 \\ .010877 \\ .011628 \\ .012333 \\ .013 \\ .013935 \\ .014809 \\ .015621 \\ .016371 \\ .017057 \\ .017678 \\ .018234 \\ .018723 \\ .018984 \\ .019066 \\ .019145 \\ .019222 \\ .019295 \\ .019366 \\ .019434 \\ .0195 \end{pmatrix} \quad i := \begin{pmatrix} .0195 \\ .0194095 \\ .0193914 \\ .0193732 \\ .01935502 \\ .0193368 \\ .0193186 \\ .019273 \\ .0192273 \\ .0191814 \\ .0191355 \\ .0190894 \\ .019062 \\ .018613 \\ .018154 \\ .017682 \\ .017197 \\ .016699 \\ .016185 \\ .015654 \\ .015105 \\ .014534 \\ .013641 \\ .012687 \\ .011672 \\ .010594 \\ .00945046 \\ .00823 \\ .006912224 \\ .005449433 \\ .00445399 \\ .0040898 \\ .003702146 \\ .003282726 \\ .0028177254 \\ .00227971366 \\ .001596919 \\ 0 \end{pmatrix}$$

FIG. 24

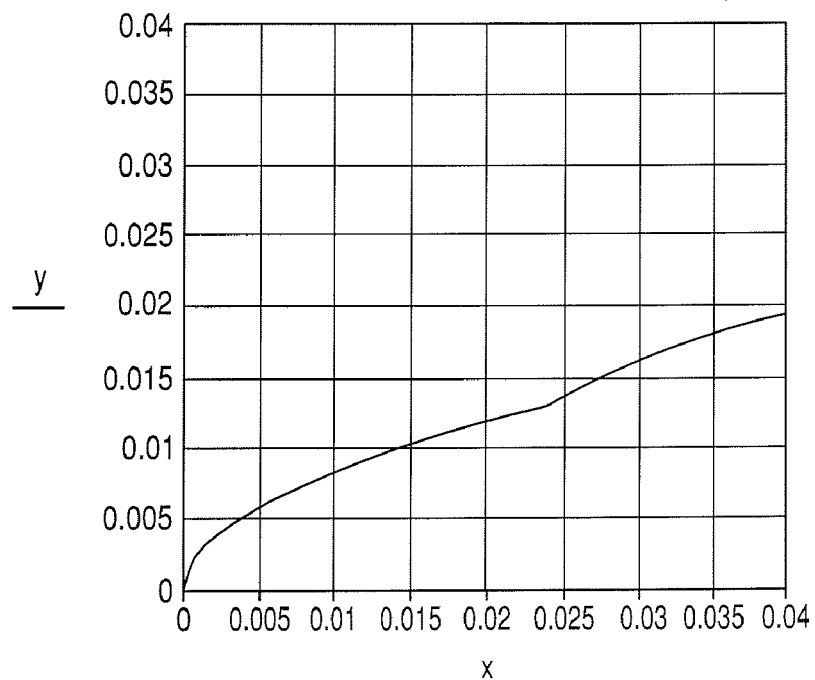
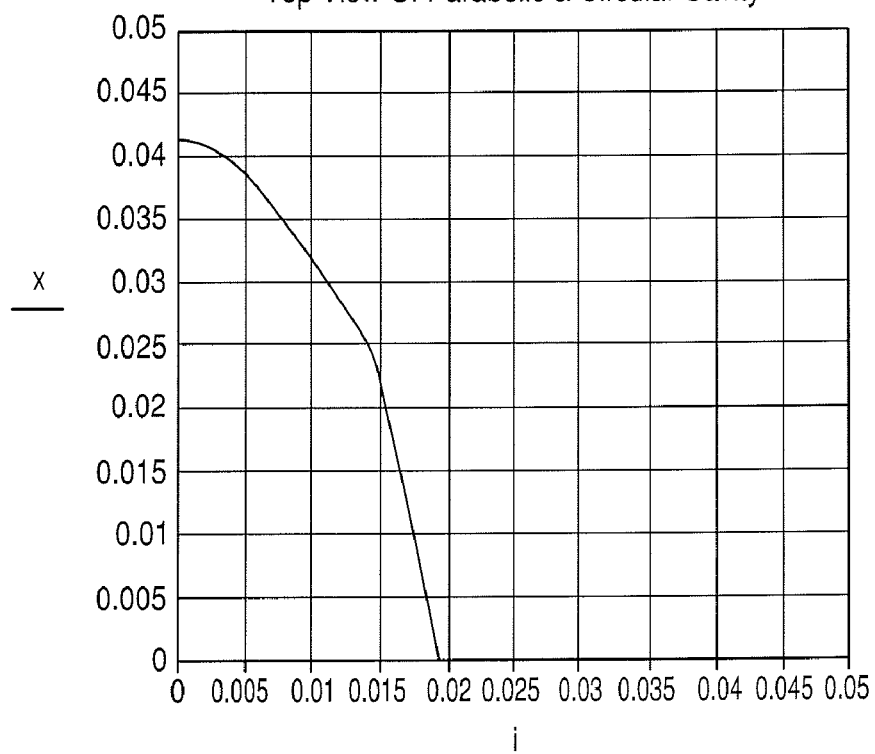
FIG. 25

Biopsy Needle Dual Cavity With Step 2    HFM 11/20/08 ro := .0195    a1 := .062    b1 := -.0225    xp := .03    yp := .0125    a := .003

$k1 := \dfrac{a1}{ro}$    $k2 := \dfrac{b1}{ro}$    $k3 := \dfrac{xp}{ro}$    $k4 := \dfrac{yp}{ro}$    $k5 := \dfrac{a}{ro}$ k1 = 3.179487    k2 = -1.153846    k3 = 1.538462    k4 = 0.641026    k5 = 0.153846

Find intersection of the curves $$r := \sqrt{(.062 - .03)^2 + ((.0195 - .003 + .0225))^2}$$

$$r = 0.050448$$

Guess $$x := .02$$

$$y := .01$$

Given $$y^2 = \dfrac{k4^2 \cdot ro \cdot x}{k3}$$

$$(x - k1 \cdot ro)^2 + (y - k2 \cdot ro)^2 = ro^2 \cdot \left[(k1 - k3)^2 + [1 - (k5 + k2)]^2\right]$$

$$\text{Find}(x,y) = \begin{pmatrix} 0.024558 \\ 0.01131 \end{pmatrix}$$

xi := .024558    yi := .01131

Check $\dfrac{k4^2 \cdot ro \cdot xi}{k3} = 1.279063 \times 10^{-4}$    $yi^2 = 1.279161 \times 10^{-4}$ $(xi - k1 \cdot ro)^2 + (yi - k2 \cdot ro)^2 = 2.545019 \times 10^{-3}$    $r^2 = 2.545 \times 10^{-3}$ Checks OK

FIG. 29

$$\beta\max := \operatorname{asin}\left(\frac{a1 - xi}{r}\right) \cdot \frac{180}{\pi} \qquad \beta\min := \operatorname{asin}\left(\frac{a1 - xp}{r}\right) \cdot \frac{180}{\pi}$$

$$\beta\max = 47.918313 \qquad \beta\min = 39.369317 \qquad N := 0,.1..1$$

$$\beta(N) := N \cdot (\beta\max - \beta\min)$$

$$\gamma(N) := \beta\min + \beta(N)$$

$$y1(N) := r \cdot \cos(\gamma(N) \cdot \deg) + b1$$

$$i(N) := \sqrt{ro^2 - y1(N)^2}$$

$$e(N) := r \cdot (\sin(\gamma(N) \cdot \deg) - \sin(\gamma(0) \cdot \deg))$$

$$\zeta(N) := \operatorname{asin}\left(\frac{i(N)}{ro}\right) \cdot \frac{180}{\pi}$$

$$A(N) := ro^2 \cdot \left[\frac{\zeta(N) \cdot \pi}{180} - \sin(\zeta(N) \cdot \deg) \cdot \cos(\zeta(N) \cdot \deg)\right]$$

$$C(N) := ro \cdot \left[1 - \frac{2}{3 \cdot A(N)} \cdot ro^2 \cdot \sin(\zeta(N) \cdot \deg)^3\right]$$

$$c(N) := ro \cdot \left[\frac{2}{3 \cdot A(N)} \cdot ro^2 \cdot \sin(\zeta(N) \cdot \deg)^3 - \cos(\zeta(N) \cdot \deg)\right]$$

$$I(N) := \frac{ro^4}{4} \cdot \left[\frac{A(N)}{ro^2} + 2 \cdot \sin(\zeta(N) \cdot \deg)^3 \cdot \cos(\zeta(N) \cdot \deg) - \frac{16}{9 \cdot A(N)} \cdot ro^2 \cdot \sin(\zeta(N) \cdot \deg)^6\right]$$

$$S(N) := \frac{-e(N) \cdot C(N)}{I(N)} \qquad s(N) := \frac{e(N) \cdot c(N)}{I(N)}$$

FIG. 30

| N = | β(N) = | γ(N) = | y1(N) = | i(N) = |
|---|---|---|---|---|
| 0 | 0 | 39.369317 | 0.0165 | 0.010392 |
| 0.1 | 0.8549 | 40.224217 | 0.016018 | 0.011121 |
| 0.2 | 1.709799 | 41.079116 | 0.015528 | 0.011796 |
| 0.3 | 2.564699 | 41.934016 | 0.015029 | 0.012425 |
| 0.4 | 3.419598 | 42.788915 | 0.014522 | 0.013014 |
| 0.5 | 4.274498 | 43.643815 | 0.014006 | 0.013567 |
| 0.6 | 5.129397 | 44.498714 | 0.013483 | 0.014088 |
| 0.7 | 5.984297 | 45.353614 | 0.012951 | 0.014578 |
| 0.8 | 6.839196 | 46.208513 | 0.012412 | 0.01504 |
| 0.9 | 7.694096 | 47.063413 | 0.011865 | 0.015475 |
| 1 | 8.548995 | 47.918313 | 0.01131 | 0.015885 |

| N = | e(N) = | ζ(N) = | A(N) = |
|---|---|---|---|
| 0 | 0 | 32.204288 | $4.225401 \cdot 10^{-5}$ |
| 0.1 | $5.78328 \cdot 10^{-4}$ | 34.770123 | $5.262438 \cdot 10^{-5}$ |
| 0.2 | $1.149403 \cdot 10^{-3}$ | 37.221803 | $6.386661 \cdot 10^{-5}$ |
| 0.3 | $1.713099 \cdot 10^{-3}$ | 39.581526 | $7.595298 \cdot 10^{-5}$ |
| 0.4 | $2.269288 \cdot 10^{-3}$ | 41.865871 | $8.885929 \cdot 10^{-5}$ |
| 0.5 | $2.817849 \cdot 10^{-3}$ | 44.087589 | $1.025638 \cdot 10^{-4}$ |
| 0.6 | $3.358658 \cdot 10^{-3}$ | 46.256742 | $1.170461 \cdot 10^{-4}$ |
| 0.7 | $3.891596 \cdot 10^{-3}$ | 48.381451 | $1.322869 \cdot 10^{-4}$ |
| 0.8 | $4.416543 \cdot 10^{-3}$ | 50.468395 | $1.482675 \cdot 10^{-4}$ |
| 0.9 | $4.933383 \cdot 10^{-3}$ | 52.523162 | $1.649692 \cdot 10^{-4}$ |
| 1 | $5.442 \cdot 10^{-3}$ | 54.550496 | $1.823733 \cdot 10^{-4}$ |

| N = | C(N) = | c(N) = | I(N) = |
|---|---|---|---|
| 0 | $1.791719 \cdot 10^{-3}$ | $1.208281 \cdot 10^{-3}$ | $2.616583 \cdot 10^{-11}$ |
| 0.1 | $2.077834 \cdot 10^{-3}$ | $1.403955 \cdot 10^{-3}$ | $4.3919 \cdot 10^{-11}$ |
| 0.2 | $2.36855 \cdot 10^{-3}$ | $1.603604 \cdot 10^{-3}$ | $6.941071 \cdot 10^{-11}$ |
| 0.3 | $2.663764 \cdot 10^{-3}$ | $1.807221 \cdot 10^{-3}$ | $1.046393 \cdot 10^{-10}$ |
| 0.4 | $2.96337 \cdot 10^{-3}$ | $2.014801 \cdot 10^{-3}$ | $1.518562 \cdot 10^{-10}$ |
| 0.5 | $3.267259 \cdot 10^{-3}$ | $2.226339 \cdot 10^{-3}$ | $2.135735 \cdot 10^{-10}$ |
| 0.6 | $3.575322 \cdot 10^{-3}$ | $2.441831 \cdot 10^{-3}$ | $2.925707 \cdot 10^{-10}$ |
| 0.7 | $3.887442 \cdot 10^{-3}$ | $2.661277 \cdot 10^{-3}$ | $3.919006 \cdot 10^{-10}$ |
| 0.8 | $4.203503 \cdot 10^{-3}$ | $2.884674 \cdot 10^{-3}$ | $5.148942 \cdot 10^{-10}$ |
| 0.9 | $4.523383 \cdot 10^{-3}$ | $3.112024 \cdot 10^{-3}$ | $6.651636 \cdot 10^{-10}$ |
| 1 | $4.846959 \cdot 10^{-3}$ | $3.343329 \cdot 10^{-3}$ | $8.466044 \cdot 10^{-10}$ |

FIG. 31

| N = | S(N) = | s(N) = |
|---|---|---|
| 0 | 0 | 0 |
| 0.1 | $-2.736105 \cdot 10^4$ | $1.848737 \cdot 10^4$ |
| 0.2 | $-3.922189 \cdot 10^4$ | $2.655481 \cdot 10^4$ |
| 0.3 | $-4.36097 \cdot 10^4$ | $2.958685 \cdot 10^4$ |
| 0.4 | $-4.42836 \cdot 10^4$ | $3.01085 \cdot 10^4$ |
| 0.5 | $-4.310761 \cdot 10^4$ | $2.93739 \cdot 10^4$ |
| 0.6 | $-4.104404 \cdot 10^4$ | $2.803178 \cdot 10^4$ |
| 0.7 | $-3.860252 \cdot 10^4$ | $2.642663 \cdot 10^4$ |
| 0.8 | $-3.605586 \cdot 10^4$ | $2.47435 \cdot 10^4$ |
| 0.9 | $-3.354901 \cdot 10^4$ | $3.308125 \cdot 10^4$ |
| 1 | $-3.115641 \cdot 10^4$ | $2.149102 \cdot 10^4$ |
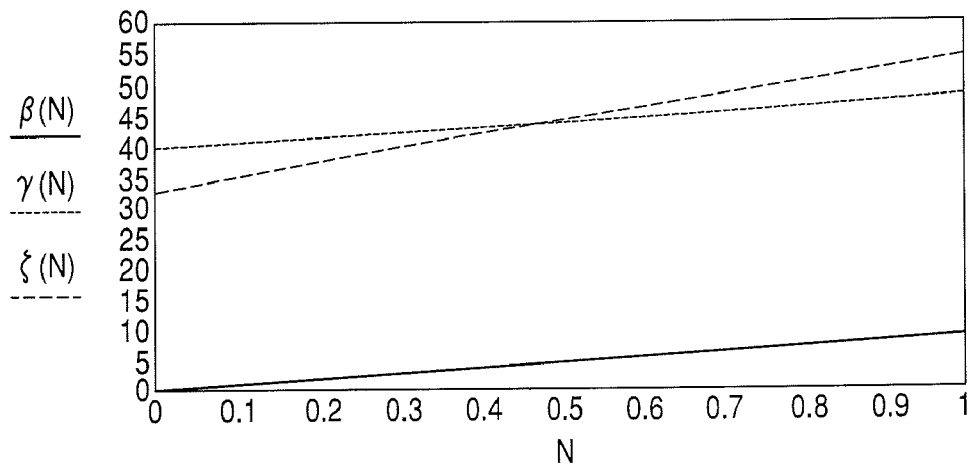
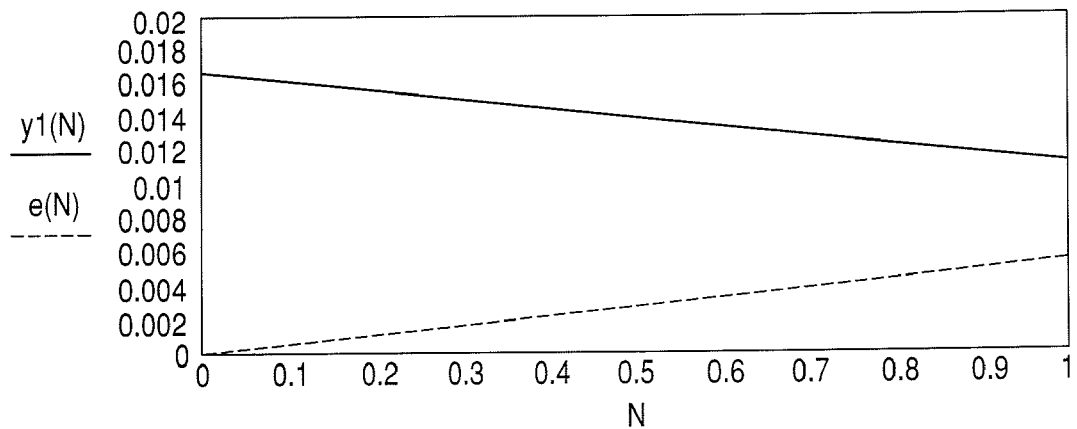
FIG. 32

Results summary $r = 0.050448$ $\beta\,\text{max} = 47.918313$ $\beta\,\text{min} = 39.369317$ $\beta(1) = 8.548995$ $\gamma(1) = 47.918313$ $y1(1) = 0.01131$ $i(1) = 0.015885$ $e(1) = 5.442 \times 10^{-3}$ $\zeta(1) = 54.550496$ $A(1) = 1.823733 \times 10^{-4}$ $C(1) = 4.846959 \times 10^{-3}$ $c(1) = 3.343329 \times 10^{-3}$ $I(1) = 8.466044 \times 10^{-10}$ $S(1) = -3.115641 \times 10^{4}$ $s(1) = 2.149102 \times 10^{4}$ $e(.35) = 1.992139 \times 10^{-3}$ $S(.35) = -4.426545 \times 10^{4}$ $s(.35) = 3.006367 \times 10^{4}$ psi/# concentrated load at the end of cantilever. Stresses in this model are significantly lower than the stresses in the 11/10/08 model Max fiber stresses in the 11/10/08 model occur at N = 0.35 & are -53,548 & 36,344 psi/#. The corresponding stresses in the 11/20/08 model occur at N = 0.35 and are -44,265 and 30,064 psi/#, respectively. Due to the uncertainty of the load distribution, the stress calculations were based on an assumed, one pound concentrated load applied at the free end of the cantilevered portion of the cavity.

FIG. 33A

Cavity Geometry
********************* ro := .0195   a1 := .062   b1 := -.0225   xp := .03   yp := .0125   a := .003

$k1 := \frac{a1}{ro}$   $k2 := \frac{b1}{ro}$   $k3 := \frac{xp}{ro}$   $k4 := \frac{yp}{ro}$   $k5 := \frac{a}{ro}$   r := .050448 k1 = 3.179487   k2 = -1.153846   k3 = 1.538462   k4 = 0.641026   k5 = 0.153846 x := 0,.0002.. .024558   xc := .024,.025.. .03   $xr := \begin{pmatrix} 0 \\ .03 \end{pmatrix}$   $yr := \begin{pmatrix} .0195 \\ .0195 \end{pmatrix}$ $y(x) := \sqrt{\frac{k4^2 \cdot ro \cdot x}{k3}}$   $yc(xc) := k2 \cdot ro + \sqrt{r^2 - (xc - k1 \cdot ro)^2}$

| x = | y(x) = | xc = | yc(xc) = |
|---|---|---|---|
| 0 | 0 | 0.024 | 0.010681 |
| $2 \cdot 10^{-4}$ | $1.020621 \cdot 10^{-3}$ | 0.025 | 0.011793 |
| $4 \cdot 10^{-4}$ | $1.443376 \cdot 10^{-3}$ | 0.026 | 0.012841 |
| $6 \cdot 10^{-4}$ | $1.767767 \cdot 10^{-3}$ | 0.027 | 0.013832 |
| $8 \cdot 10^{-4}$ | $2.041241 \cdot 10^{-3}$ | 0.028 | 0.014769 |
| $1 \cdot 10^{-3}$ | $2.282177 \cdot 10^{-3}$ | 0.029 | 0.015658 |
| $1.2 \cdot 10^{-3}$ | $2.5 \cdot 10^{-3}$ | 0.03 | 0.0165 |
| $1.4 \cdot 10^{-3}$ | $2.700309 \cdot 10^{-3}$ | | |
| $1.6 \cdot 10^{-3}$ | $2.886751 \cdot 10^{-3}$ | | |
| $1.8 \cdot 10^{-3}$ | $3.061862 \cdot 10^{-3}$ | | |
| $2 \cdot 10^{-3}$ | $3.227486 \cdot 10^{-3}$ | | |
| $2.2 \cdot 10^{-3}$ | $3.385016 \cdot 10^{-3}$ | | |
| $2.4 \cdot 10^{-3}$ | $3.535534 \cdot 10^{-3}$ | | |
| $2.6 \cdot 10^{-3}$ | $3.6799 \cdot 10^{-3}$ | | |
| $2.8 \cdot 10^{-3}$ | $3.818813 \cdot 10^{-3}$ | | |
| $3 \cdot 10^{-3}$ | $3.952847 \cdot 10^{-3}$ | | |

FIG. 34

Side view of the biopsy needle at approximately 100 x full size. Needle center line is at the horizontal axis $$i(x) := \sqrt{ro^2 - y(x)^2} \qquad ic(xc) := \sqrt{ro^2 - yc(xc)^2} \qquad x := 0, .002 .. .024$$

$$xc := .024, .025 ... .03$$

| x = | i(x) = |
|---|---|
| 0 | 0.0195 |
| 2·10⁻³ | 0.019231 |
| 4·10⁻³ | 0.018958 |
| 6·10⁻³ | 0.018682 |
| 8·10⁻³ | 0.018401 |
| 0.01 | 0.018115 |
| 0.012 | 0.017826 |
| 0.014 | 0.017531 |
| 0.016 | 0.017231 |
| 0.018 | 0.016926 |
| 0.02 | 0.016616 |
| 0.022 | 0.016299 |
| 0.024 | 0.015977 |

| xc = | yc(xc) = | ic(xc) = |
|---|---|---|
| 0.024 | 0.010681 | 0.016314 |
| 0.025 | 0.011793 | 0.01553 |
| 0.026 | 0.012841 | 0.014675 |
| 0.027 | 0.013832 | 0.013745 |
| 0.028 | 0.014769 | 0.012733 |
| 0.029 | 0.015658 | 0.011623 |
| 0.03 | 0.0165 | 0.010392 |

Top view of the tip of the biopsy needle at approximately 100 x full size. Needle center line is on the vertical axis.

BIOPSY NEEDLE

CROSS REFERENCE TO RELATED APPLICATIONS

This application is a continuation-in-part of U.S. application Ser. No. 11/228,466, entitled "Biopsy Needle", which was filed Sep. 19, 2005, which is currently pending. This application is based upon U.S. Provisional Application Ser. No. 60/610,542, entitled "BIOPSY NEEDLE", which was filed Sep. 17, 2004.

BACKGROUND OF THE INVENTION

1. Field of the Invention

The invention relates to a biopsy needle. More particularly, the invention relates to a biopsy needle having a sample recess shaped and dimensioned to optimize operation of the biopsy needle. The invention also relates to a method for forming the recess.

2. Description of the Prior Art

Biopsy needles are currently available in gauges ranging from 14 to 20. The biopsy samples are obtained using various methods. One of the commercially available designs employs a solid, pointed cannula inside of a slip-fitted outer cannula with a beveled leading end. The solid inner cannula contains a rectangular cavity, which collects the biopsy sample. The biopsy sample is removed from the tissue by inserting the biopsy needle into the tissue, uncovering the collection portion, that is, the rectangular cavity, and firing the outer cannula forward quickly using a spring. The portion of the tissue in the region of the sample collection rectangular cavity is torn from the surrounding tissue and collected in the rectangular cavity. Biopsy sample collection using this "brute force" approach results in trauma to the patient. A need exists, therefore, for a biopsy needle that obtains the desired sample by cutting rather than tearing the sample from the surrounding tissue.

SUMMARY OF THE INVENTION

It is, therefore, an object of the present invention to provide a biopsy needle including an outer cannula and an inner cannula. The inner cannula includes a distal end and a proximal end, the outer cannula being shaped and dimensioned to closely circumscribe the inner cannula for movement relative thereto. The inner cannula further includes a sample recess at its distal end, the sample recess including a dual cavity recess composed of a first cavity intersecting with a second cavity, wherein the first cavity has a first shape and the second cavity has a second shape.

It is also an object of the present invention to provide a biopsy needle wherein the first shape is different from the second shape.

It is another object of the present invention to provide a biopsy needle wherein the first cavity has a parabolic shape and the second cavity has a circular shape.

It is also an object of the present invention to provide a biopsy needle wherein second cavity is defined by the following relationship $$ro := .0195 \quad xi := .024 \quad yi := .013 \quad a1 := .05 \quad b1 := -.03$$

$$k1 := \frac{xi}{ro}, \quad k2 := \frac{yi}{ro}, \quad k3 := \frac{a1}{ro}, \quad k4 := \frac{b1}{ro}$$

-continued $$r := \sqrt{(a1 - xi)^2 + (yi - b1)^2}$$

$r = 0.050249$ radius of the circular portion $$\beta\min := a\cos\left(\frac{ro - b1}{r}\right) \cdot \frac{180}{\pi}$$

$\beta\min = 9.907498$ $$\beta\max := a\sin\left(\frac{a1 - xi}{r}\right) \cdot \frac{180}{\pi}$$

$\beta\max = 31.159305$ $L := a1 - r \cdot \sin(\beta\min \cdot deg)$ $L = 0.041354$ Total cavity length where,
ro=radius of the inner cannula of the biopsy needle
xi=x coordinate of the parabolic/circular intersection
yi=y coordinate of the parabolic/circular intersection
a1=x coordinate of the center of curvature of the circular portion
b1=y coordinate of the center of curvature of the circular portion
r=the radius of the circular cavity
$\beta\min$=the minimum value of the angle $\beta$
$\beta\max$=the maximum value of the angle $\beta$
L=the overall length of the biopsy sample recess.

It is another object of the present invention to provide a biopsy needle wherein properties of the first cavity are calculated according to the following relationships using the equations for A(n), C(n), c(n) and I(n), which is the moment of inertia of the parabolic cavity,
A(n)=transverse area of the cantilever sector
C(n)=distance from the neutral axis (NA) to the extreme fiber above the NA
c(n)=distance from the NA to the extreme fiber below the NA
I(n)=moment of inertia of the area sector, A(n), about the NA $$A(n) := ro^2 \cdot \left(\frac{\alpha(n) \cdot \pi}{180} - \sin(\alpha(n) \cdot deg) \cdot \cos(\alpha(n) \cdot deg)\right)$$

$$C(n) := ro \cdot \left(1 - \frac{2 \cdot ro^2 \cdot \sin(\alpha(n) \cdot deg)^3}{3 \cdot A(n)}\right)$$

$$c(n) = ro \cdot \left(\frac{2 \cdot ro^2 \cdot \sin(\alpha(n) \cdot deg)^3}{3 \cdot A(n)} - \cos(\alpha(n) \cdot deg)\right)$$

$$I(n) := \frac{ro^4}{4} \cdot$$

$$\left(\frac{A(n)}{ro^2} + 2 \cdot \sin(\alpha(n) \cdot deg)^3 \cdot \cos(\alpha(n) \cdot deg) - \frac{16 \cdot ro^2 \cdot \sin(\alpha(n) \cdot deg)^6}{9 \cdot A(n)}\right)$$

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 8, 8A, 9, 9A, 10 and 10A are various studies of the biopsy needle in accordance with the present invention.

FIGS. 11 through 16 are biopsy needle design charts for selected 20, 14 and 18 GA needles in accordance with the present invention.

FIGS. 22, 23, 24, 25, 26 and 27 show various graphs and charts relating to the design of the biopsy needle in accordance with the embodiment shown in FIGS. 19, 20 and 21.

FIGS. 29-36 are various graphs and charts relating to the design of the biopsy needle in accordance with the embodiment shown in FIG. 28.

DESCRIPTION OF THE PREFERRED EMBODIMENTS

Figure 1:
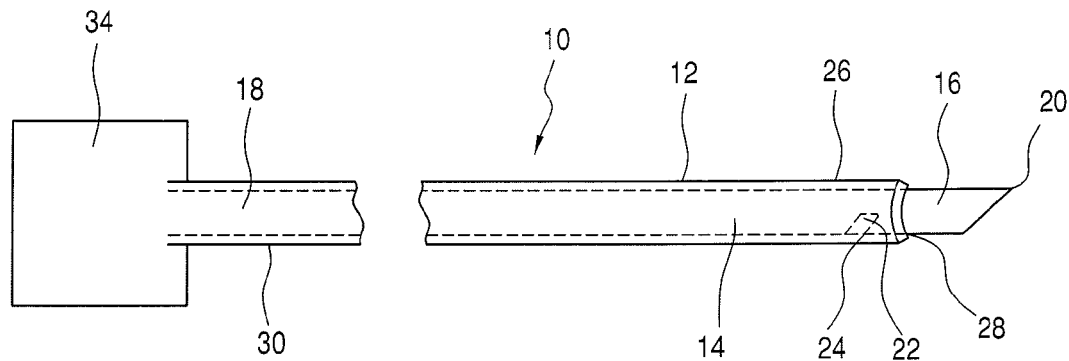
FIG. 1 is a side view of the present biopsy needle.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 through 7, a biopsy needle 10 in accordance with the present invention is disclosed. The biopsy needle 10 generally includes a cutting outer cannula 12 that surrounds a solid inner cannula 14. As those skilled in the art will certainly appreciate, the cutting outer cannula 12 is shaped and dimensioned to fit about the inner cannula 14 in a manner permitting relative movement with the removal of core biopsy samples upon proper actuation of the biopsy needle 10. With this in mind, the outer cannula 12 fits closely about the inner cannula 14 to facilitate cutting of the sample tissue as the outer cannula 12 is moved relative to the inner cannula 14; that is, the outer cannula 12 is slip-fit over the inner cannula 14.

In general, the inner cannula 14 includes a distal end 16 and a proximal end 18. The distal end 16 is provided with a distal tip 20 and a sample recess 22 having a cutting edge 24. The distal tip 20 is a traditional pointed tip adapted to easily move through tissue with the creation of limited trauma.

As to the outer cannula 12, it also includes a distal end 26 having a sharpened distal tip 28 and a proximal end 30. The outer cannula 12 has a beveled, 360-degree cutting edge 32 at its distal tip 28. The leading, cutting edge 32 of the outer cannula 12 is beveled for a full 360 degrees. The outer cannula 12 is suitably spring driven to slide axially along the inner cannula 14 when triggered by the physician. The cutting edges 24, 32 of the inner cannula 14 and outer cannula 12 remove the biopsy sample by cutting the sample in scissor-like fashion as the spring-driven, outer cannula 12 slides axially along the inner cannula 14.

The proximal end 18 of the inner cannula 14 and the proximal end 30 of the outer cannula 12 are respectively coupled to an actuation mechanism 34 controlling movement of the outer cannula 12 relative to the inner cannula 14. In accordance with a preferred embodiment, the actuation mechanism 34 is a spring biased actuation mechanism as disclosed in U.S. Pat. No. 5,425,376 to Banys et al., which is incorporated herein by reference, although other actuation mechanisms may certainly be used without departing from the spirit of the present invention.

The biopsy needle 10 is preferably made of medical grade stainless steel although those skilled in the art will appreciate it may be manufactured from other materials without departing from the spirit of the present invention.

Figure 2:
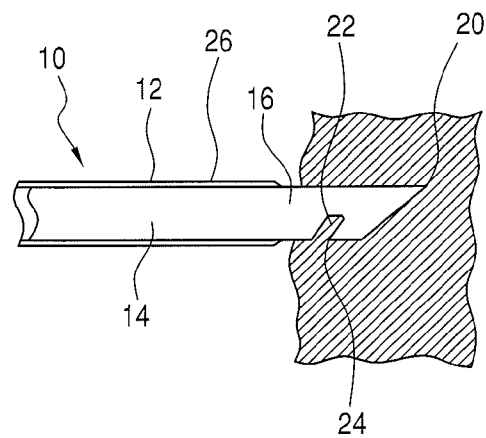
FIGS. 2 and 3 are cross sectional views of the biopsy needle showing operation thereof.
Figure 3:
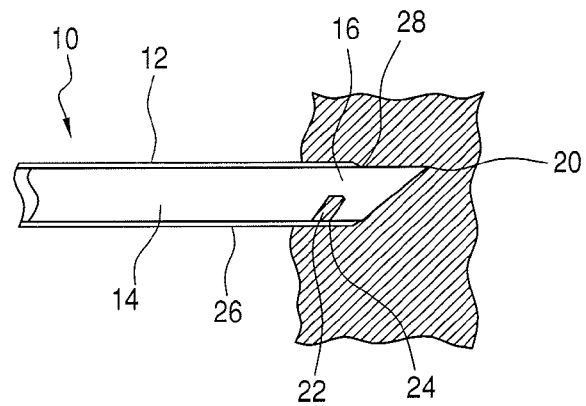

In use, and with reference to FIGS. 2 and 3, the biopsy needle 10 is positioned at a predetermined location where it is desired to obtain a biopsy sample from a patient. The distal end 16 of the inner cannula 14 is exposed with the sample recess 22 exposed for positioning of a biopsy sample therein. Because of the resilience of the tissue at the predetermined location, a small portion of tissue is forced within the sample recess 22. The outer cannula 12 is then selectively actuated for movement toward the distal end 16 of the inner cannula 14 in a manner which cuts the tissue such that a small sample is retained within the sample recess 22. With the tissue maintained in the sample recess 22 between the inner surface of the outer cannula 12 and the outer surface of the inner cannula 14, the biopsy needle 10 may be removed from the patient for retrieval of the tissue sample maintained in the sample recess 22.

As briefly discussed above, the sample recess 22 is formed at the distal end 16 of the inner cannula 14. The sample recess 22 includes a forward wall 22a, a base 22b and a rearward wall 22c. The forward wall 22a includes a three dimensional, integral, biopsy sample cutting edge 24 which faces 180 degrees from the distal tip 20 of the inner cannula 14.

Figure 4:
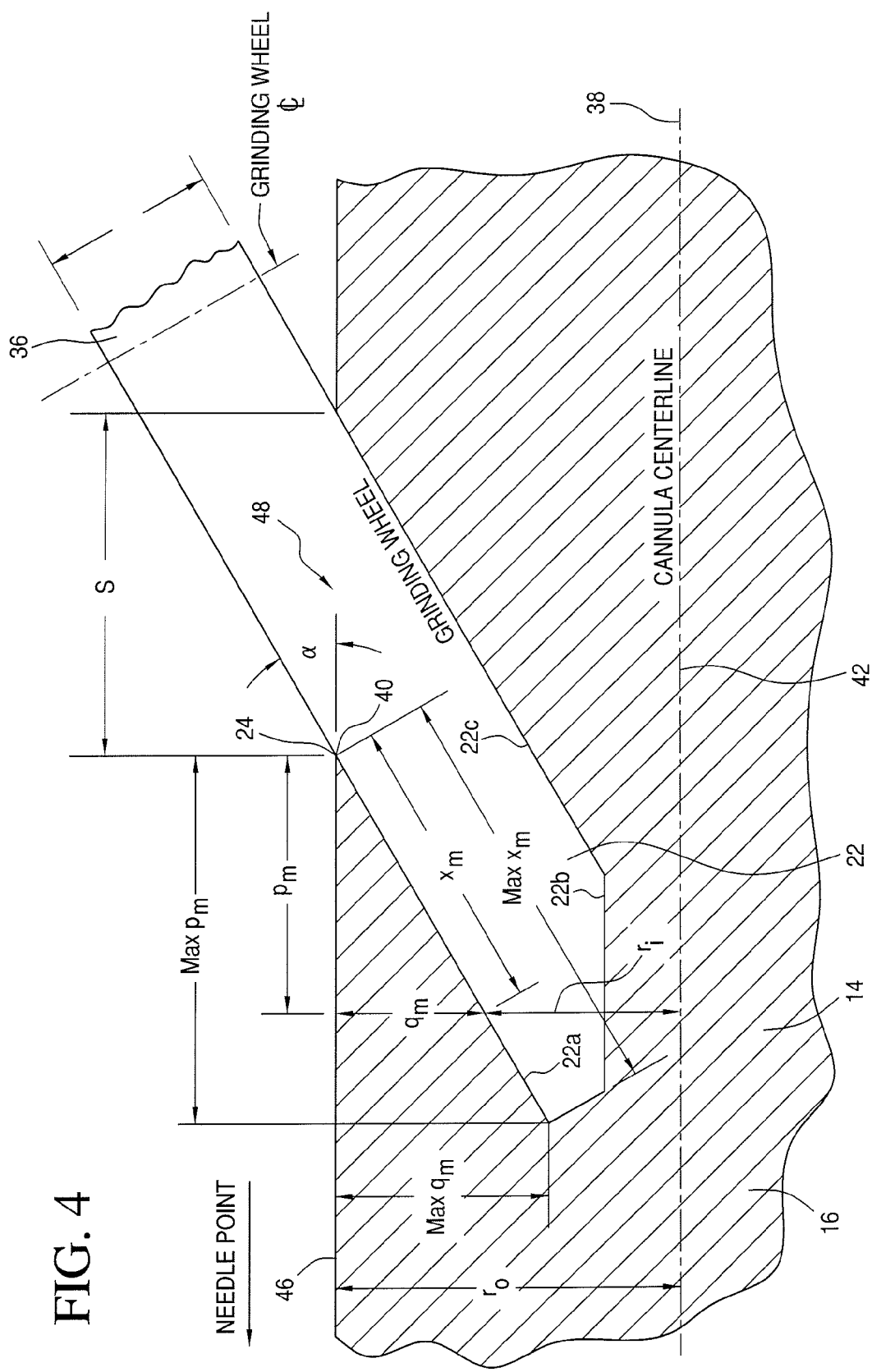
FIG. 4 is a detailed cross sectional view of the inner cannula about a plane symmetrically bisecting the sample recess.
Figure 5:
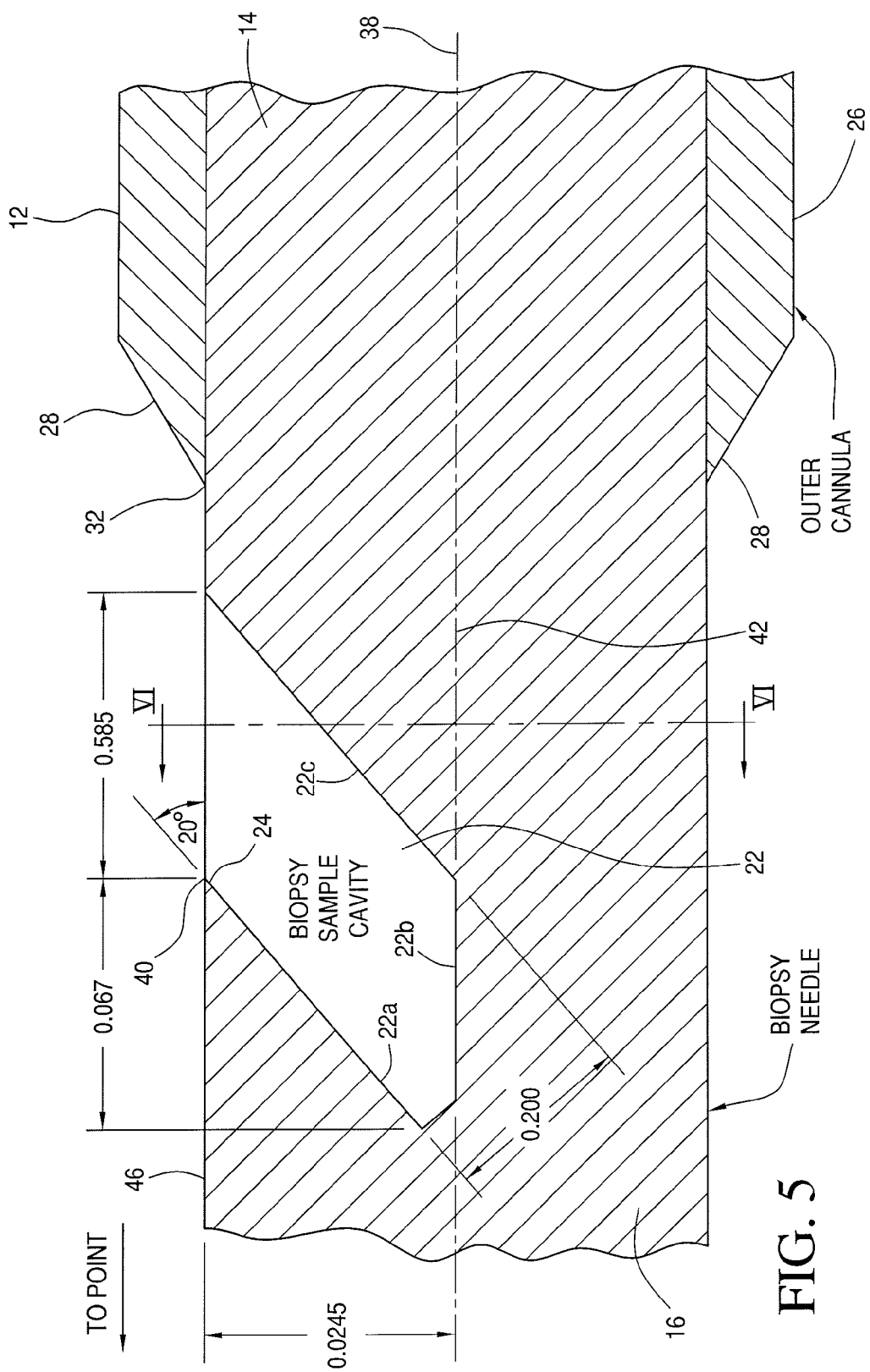
FIG. 5 is a detailed cross sectional view of the biopsy needle about a plane symmetrically bisecting the sample recess.

Referring to FIGS. 4 and 5, the method for producing the inner cannula 14 cutting edge 24 on the biopsy needle 10 is shown. The cutting edge 24 is located a short distance behind the distal tip 20 of the inner cannula 14. The cutting edge 24 is produced by grinding the biopsy needle inner cannula 14 with a circular grinding wheel 36, which has been contoured to the geometry shown in FIG. 4. The axis of rotation of the grinding wheel 36 is set at a small angle, $\alpha$, off the perpendicular to the longitudinal axis 38 of the biopsy needle, and in particular, the inner cannula 14. The grinding process produces the three-dimensional, "U" shaped cutting edge 24 at the outer diameter (OD), or outside surface, 46 of the biopsy needle inner cannula 14 as the grinding wheel 36 moves through the inner cannula 14 in a direction transverse to the longitudinal axis of the biopsy needle 10.

The geometry of the "U" shaped cutting edge 24 depends on the values of the design parameters used. For any selected inner cannula 14 outer diameter (OD), the closed end of the "U" shaped cutting edge 24 can be ground to produce a relatively broad or a relatively sharp point 40 by changing the grinding angle, $\alpha$, shown in FIG. 4.

A mathematical analysis was conducted to derive the equations necessary to design the three-dimensional "U" shaped cutting edge 24 for the inner cannula 14 of the biopsy needle 10. FIG. 4 shows the grinding wheel 36 at some arbitrary depth, $r_i$, in the biopsy needle inner cannula 14 wherein $r_i$ is the distance from the centerline 42 of the inner cannula 14 to which the grinding wheel 36 penetrates while forming the sample recess 22 (which may also be considered the base 22b of the sample recess 22). The points designated by the parameters xn, pn, qn define the "U" shaped, biopsy needle cutting edge 24 when viewed perpendicular to the longitudinal, transverse axis of the inner cannula 14 (as shown with reference to FIG. 4). By way of explanation xn is the actual length position along the sample recess 22, pn is the length position of the sample recess 22 relative to the cutting edge 24 along a line substantially parallel to the inner cannula 14 longitudinal axis and qn is the depth position of the sample recess 22 relative to the apex of the arc defined by the cutting edge 24.

When viewed from the perspective shown in FIG. 4, the "U" shaped profile appears to be merely a taper. However, when viewed from above the inner cannula 14 (see FIG. 7), the "U" shaped geometry is clearly evident. The three-dimensional, "U" shaped geometry is, of course, created by the intersection of the flat outer surface of the grinding wheel 36 with the outside surface 46 of the biopsy needle inner cannula 14.

Figure 6:
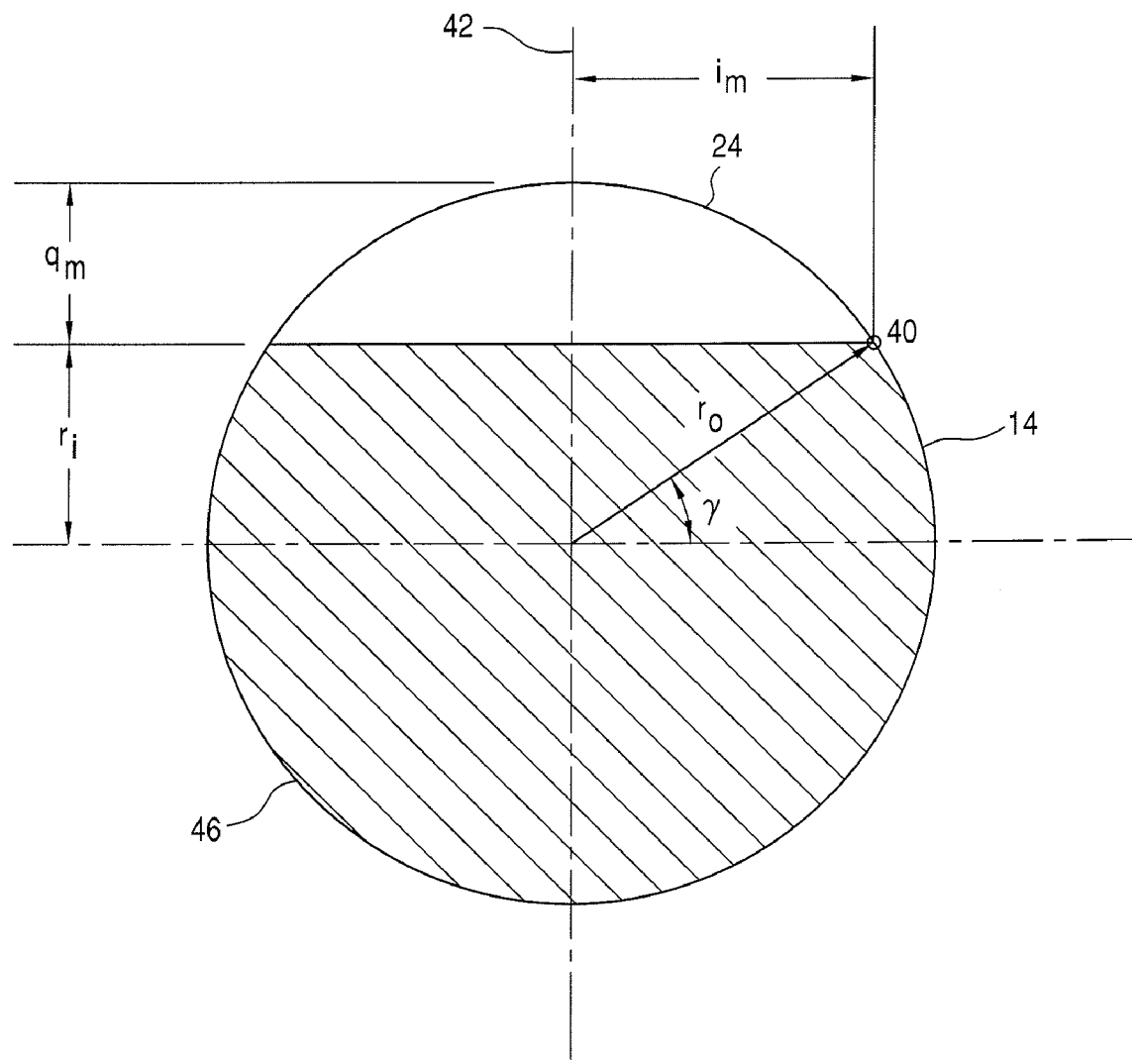
FIG. 6 is a cross sectional view along the line VI-VI in FIG. 5.
Figure 7:
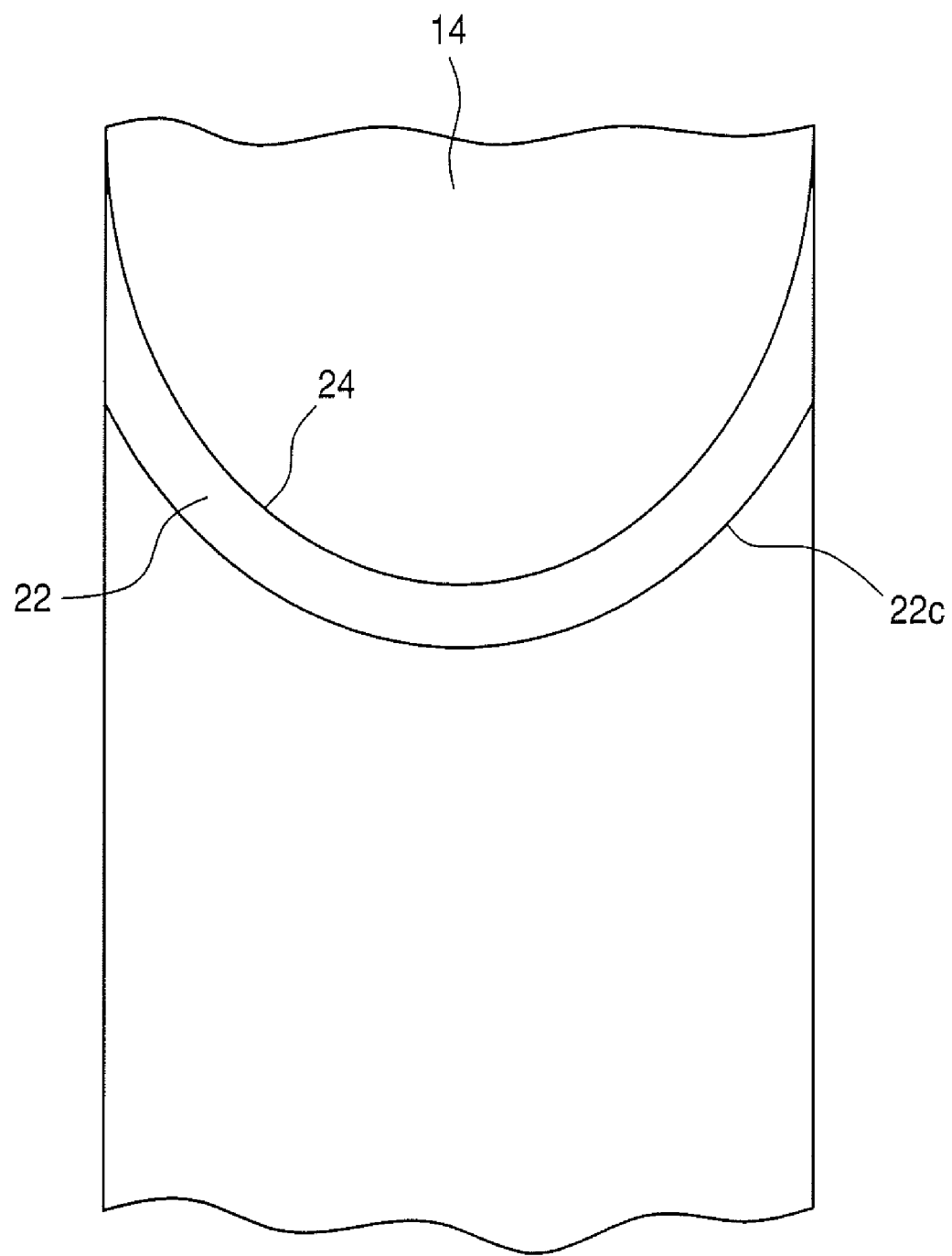
FIG. 7 is a top view of the inner cannula.

Referring to FIGS. 4, 5 and 6, one can write the following equations for the biopsy needle cavity:

$$qn(\gamma) := ro \cdot (1 - \sin(\gamma \cdot deg))$$

$$xn(\gamma) := \frac{ro \cdot (1 - \sin(\gamma \cdot deg))}{\sin(\alpha \cdot deg)}$$

$$pn(\gamma) := \frac{ro \cdot (1 - \sin(\gamma \cdot deg))}{\tan(\alpha \cdot deg)}$$

$$in(\gamma) := ro \cdot \cos(\gamma \cdot deg)$$

$$ri(\gamma) := ro \cdot \sin(\gamma \cdot deg)$$

where,
α is an angle at which the cutting edge is formed;
xn is an actual length position along the biopsy sample cavity;
pn is a length position of the biopsy sample cavity relative to the cutting edge along a line substantially parallel to an inner cannula longitudinal axis;
qn is a depth position of the biopsy sample cavity relative to an apex of an arc defined by the cutting edge;
in is the distance from the centerline 42 of the transverse cross section of the inner cannula to the point of intersection of the grinding wheel 36 (or the sharp point of the cutting edge 24) and the OD of the inner cannula 14 (i.e., point 40);
γ is an angle measured from a horizontal cross sectional centerline of the biopsy needle to the point of contact 40; and
ri is the distance from the horizontal cross section centerline to point 40.

FIG. 6 shows the transverse cross section of the biopsy needle inner cannula 14. The distance in is the distance from the centerline 42 of the transverse cross section of the inner cannula 14 to the point of intersection of the grinding wheel 36 (or the sharp point 40 of the cutting edge 24) and the OD of the inner cannula 14. The value of in can be written:

$$in(\gamma) := ro \cdot \cos(\gamma \cdot deg)$$

Figure 10A:
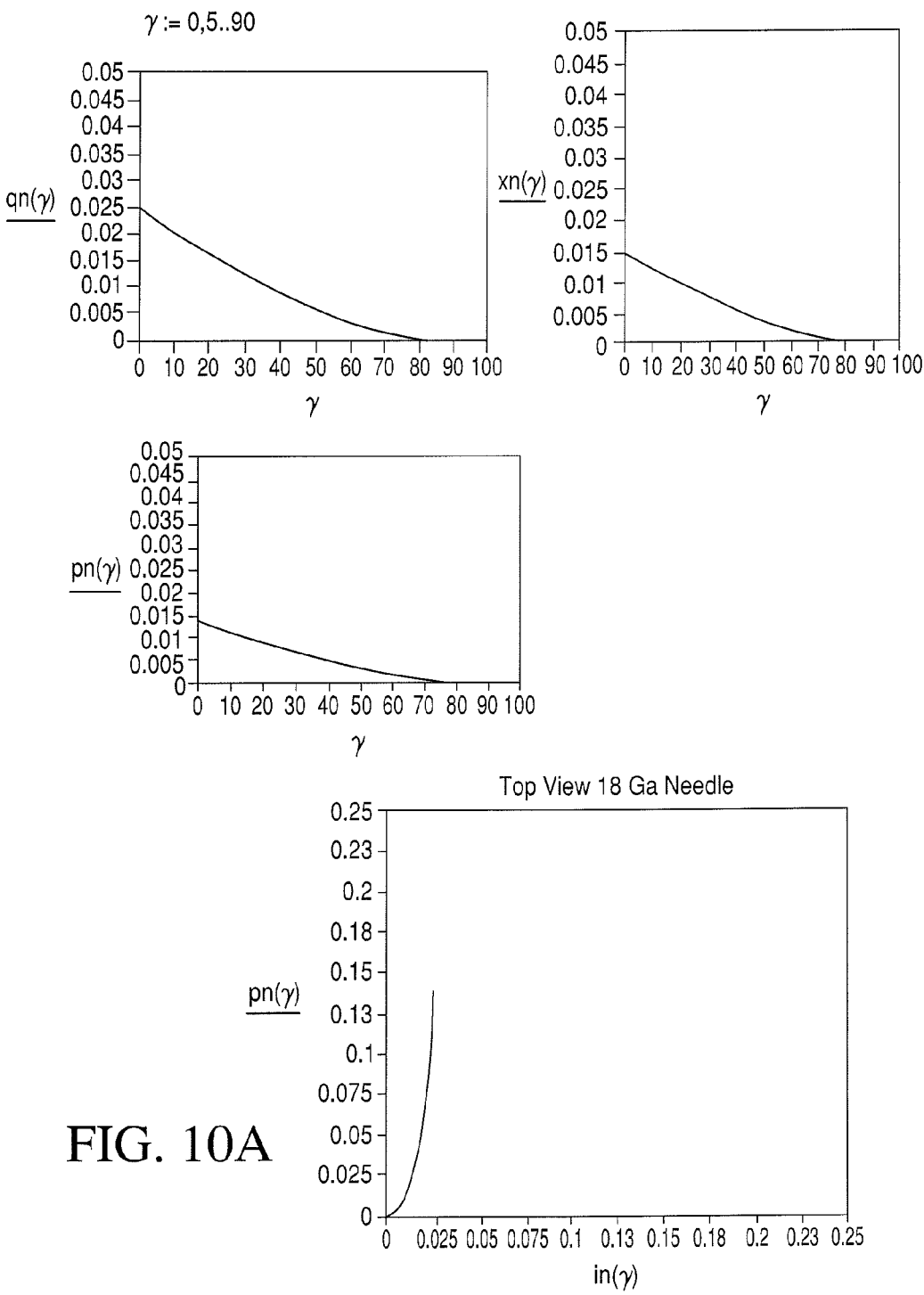
Figure 12:
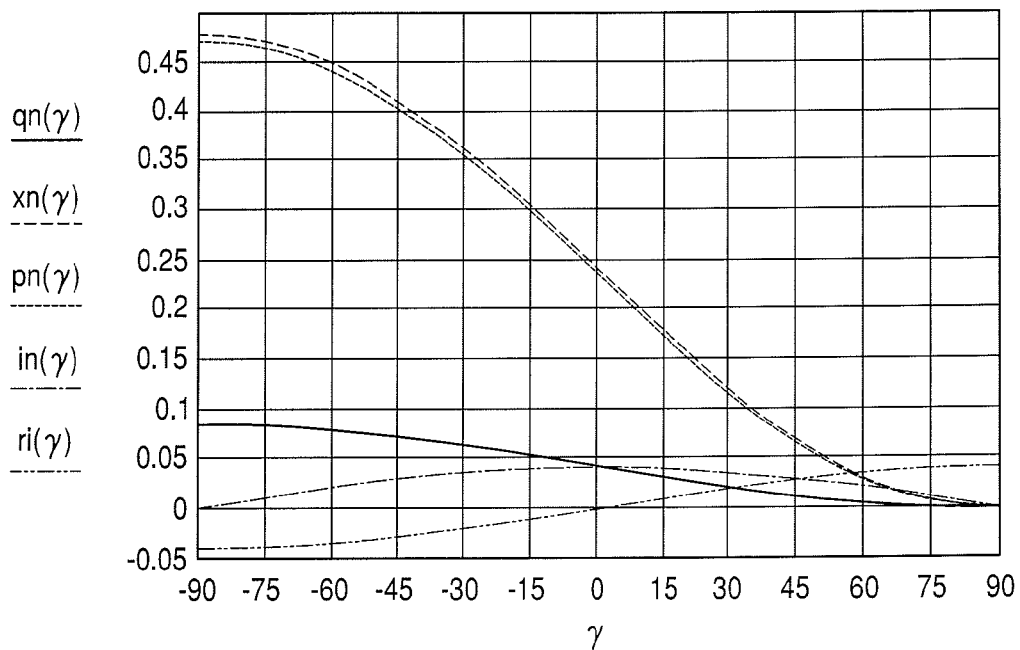
Figure 13:
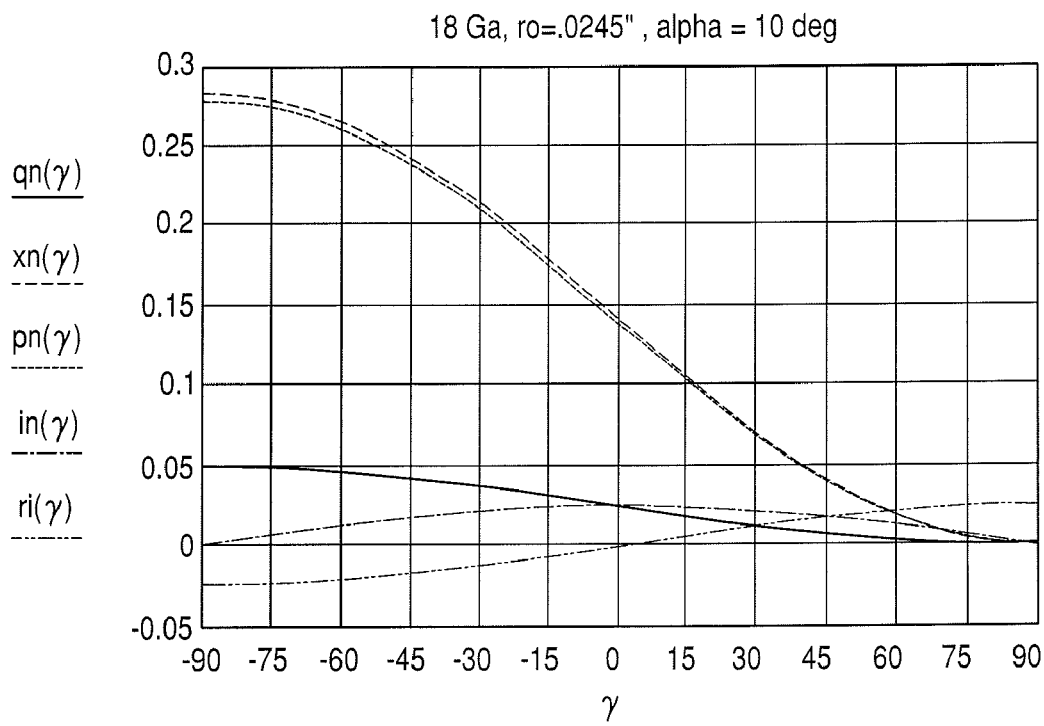
Figure 15:
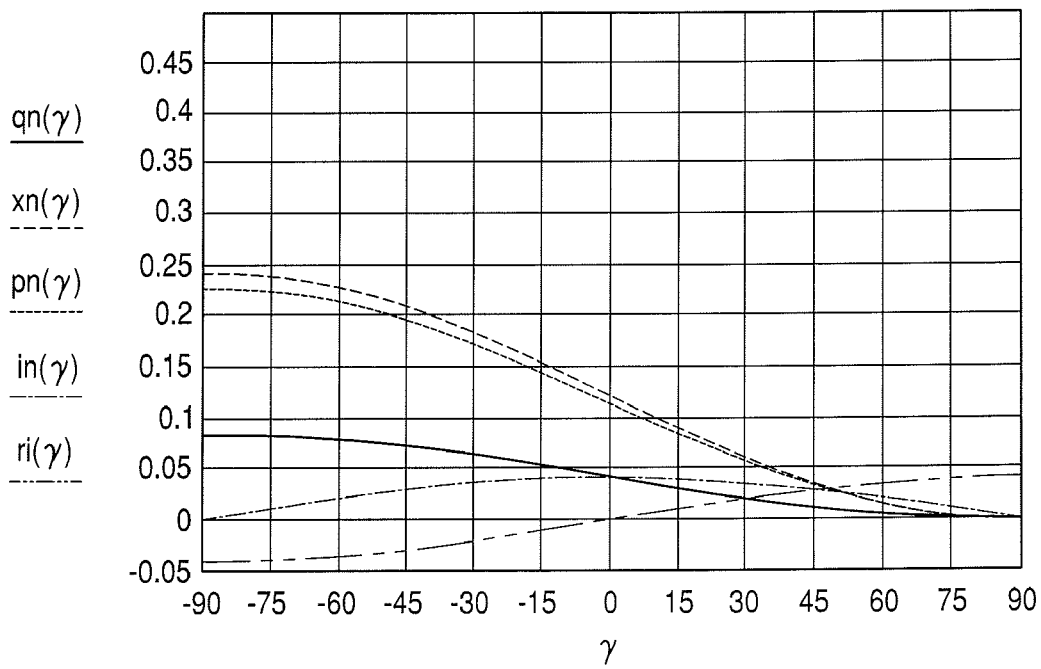
Figure 16:
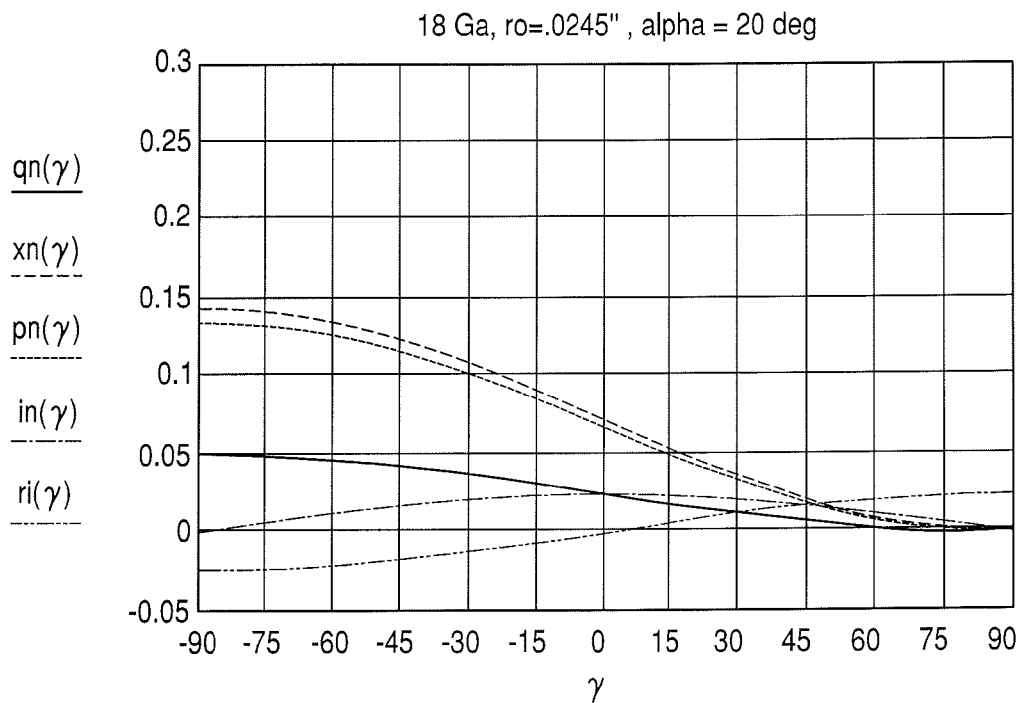

From pn, qn, and in we can plot the three dimensional geometry of the "U" shaped cutting edge 24 on the inner cannula 14. For our purposes, a two-dimensional plot of pn vs. in shows the geometry of the "U" shaped cutting edge when viewed from above the inner cannula 14. The variation in cutting edge geometry is readily apparent from a plot of pn vs. in(γ) (see FIGS. 8, 9 and 10). The length of the biopsy sample cavity, S, is:

$$S = \frac{h}{\sin\alpha}$$

where,
h is the thickness of the grinding wheel 36 and/or the resulting opening distance 48 of the biopsy sample cavity 22.
Note that the length of the biopsy cavity, S, may be increased by changing the width of the grinding wheel, h, or by traversing the grinding wheel in an axial direction with respect to the biopsy needle centerline. Further, the rearward facing portion of the grinding wheel may be dressed (i.e., contoured) to provide a geometry on the rear of the biopsy needle cavity which will tend to prevent the biopsy sample from being pulled out of the biopsy sample cavity by the axial, relative sliding motion of the inner and outer cannula as the biopsy sample as being excised.

Now that a basic understanding of the sample recess geometry is appreciated, the preferred embodiments which optimize operation in accordance with the present invention are disclosed. To demonstrate the use of the design equations, the geometry of the biopsy needle "U" shaped cutting edge was calculated for three needle gauges, namely 20 Ga, 18 Ga, and 14 Ga. The 20 to 14 Ga range covers the range of gauges currently being used, with particularly heavy usage being noted with regard to the 18 Ga size. In the three examples given below, the grinding wheel penetration is approximately to the centerline of the inner cannula. This was accomplished by setting the parameter γ to zero in the design equations. The design parameters and the results are listed below:

| Example 1 (20 Ga) | Example 2 (14 Ga) | Example 3 (18 Ga) |
|---|---|---|
| ro = 0.0175" | ro = 0.0415" | ro = 0.0245" |
| γ = 0 | γ = 0 | γ = 0 |
| h = 0.20 | h = 0.20 | h = 0.20 |
| α = 10° | α = 10° | α = 10° |
| xn = 0.1008 | xn = 0.2390 | xn = 0.1411 |
| pn = 0.0992 | pn = 0.2354 | pn = 0.1389 |
| qn = 0.0175 | qn = 0.0415 | qn = 0.0245 |
| in = 0.0175 | in = 0.0415 | in = 0.0245 |
| ri = 0 | ri = 0 | ri = 0 |

The pn vs. in curves for the three examples showing the geometry of the cutting edge when viewed from above the inner cannula of the biopsy needle are given in FIGS. 8, 9 and 10, respectively.

The width of the biopsy sample cavity for all three examples is 1.151 inches.

To demonstrate the influence of the angle, α, in the three examples given above, the value of angle α was changed from 10° to 20° and the results were recalculated in all three examples. The results are as follows:

| Example 1 (20 Ga) | Example 2 (14 Ga) | Example 3 (18 Ga) |
|---|---|---|
| xn = 0.0512" | xn = 0.1213" | xn = 0.0716" |
| pn = 0.0481" | pn = 0.1140" | pn = 0.0673" |
| qn = 0.0175" | qn = 0.0415" | qn = 0.0245" |
| in = ±0.0175" | in = ±0.0415" | in = ±0.0245" |
| ri = 0 | ri = 0 | ri = 0 |

The length of the sample cavity, S, is 0.585" for all three examples. The pn vs. in curves are given in FIGS. 8A, 9A and 10A for α=20°.

The results for all of the examples are summarized below:

| Ga | α, ° | xn" | pn" | qn" | in" | S | ri |
|---|---|---|---|---|---|---|---|
| 20 | 10 | 0.1008 | 0.0992 | 0.0175 | 0.0175 | 1.151 | 0 |
| 20 | 20 | 0.0512 | 0.0481 | 0.0175 | 0.0175 | 0.585 | 0 |
| 14 | 10 | 0.2399 | 0.2354 | 0.0145 | 0.0145 | 1.151 | 0 |
| 14 | 20 | 0.1213 | 0.1140 | 0.0145 | 0.0145 | 0.585 | 0 |
| 18 | 10 | 0.1411 | 0.1389 | 0.0245 | 0.0245 | 1.151 | 0 |
| 18 | 20 | 0.07163 | 0.0673 | 0.0245 | 0.0245 | 0.585 | 0 |

From the results above, one sees that increasing the angle, α, results in smaller values of max pn while maintaining the same values for max qn. The result is a stiffening of the cutting edge as α increases. In addition, the size of biopsy sample recess, S, decreases as a increases.

In the examples given, the value of γ was zero which brings the depth of the grind to the centerline of the inner cannula. Selecting values of γ greater than zero produces a grind which is above the centerline of the inner cannula which results in a biopsy needle point which is more resistant to bending.

Note that in the examples selected herein, the grinding depth was halfway through the inner cannula (i.e., γ=0). It is, however, contemplated other grinding depths may be used to produce the cutting edge desired by selecting a value of γ between −90° to +90°. Design curves for 20, 14 and 18 Ga biopsy needles with angles α=10° and α=20° are shown in FIGS. 11-16 for all values of γ between −90° and +90° for comparison purposes. Care should be taken when using negative values of the angle γ since bending and/or fracture of the needle tip may occur. Note that FIGS. 11-16 provide a simple method for evaluating various design geometries since the selected parameters may be obtained directly from FIGS. 11-16.

In operation, and as briefly discussed above, the biopsy needle 10 is inserted to the depth required and the outer cannula 12 is withdrawn and cocked. The portion of the tissue to be excised is in the region of the biopsy sample recess 22. When the outer cannula 12 is fired, the outer cannula 12 moves toward the distal tip 20 of the inner cannula 14. The portion of the tissue protruding into the biopsy sample recess 22 is cut off by the two cutting edges 24, 32 and is collected in the biopsy sample recess 22.

Figure 17:
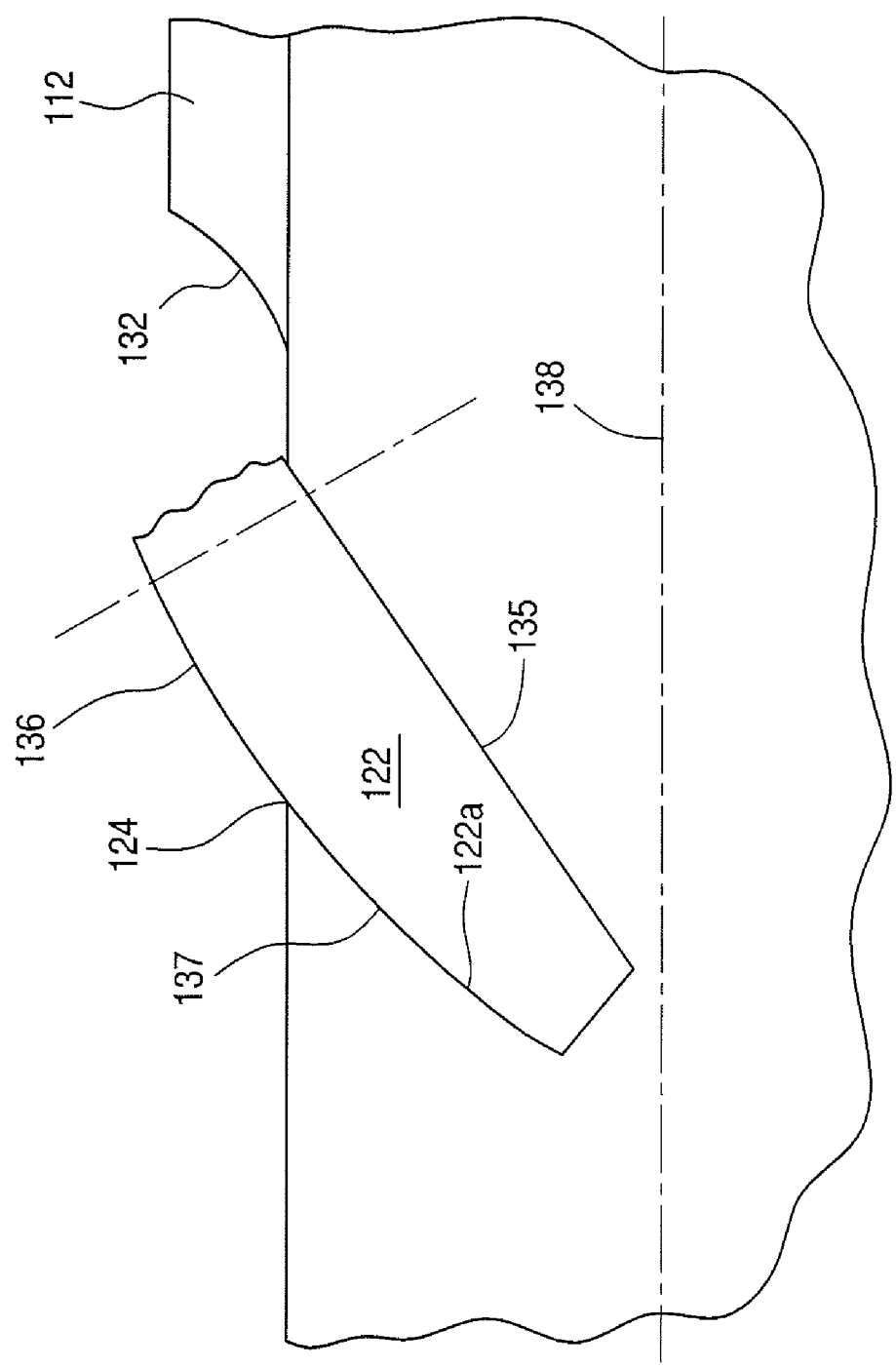
FIG. 17 is a cross sectional view in accordance with an alternate embodiment.
Figure 18:
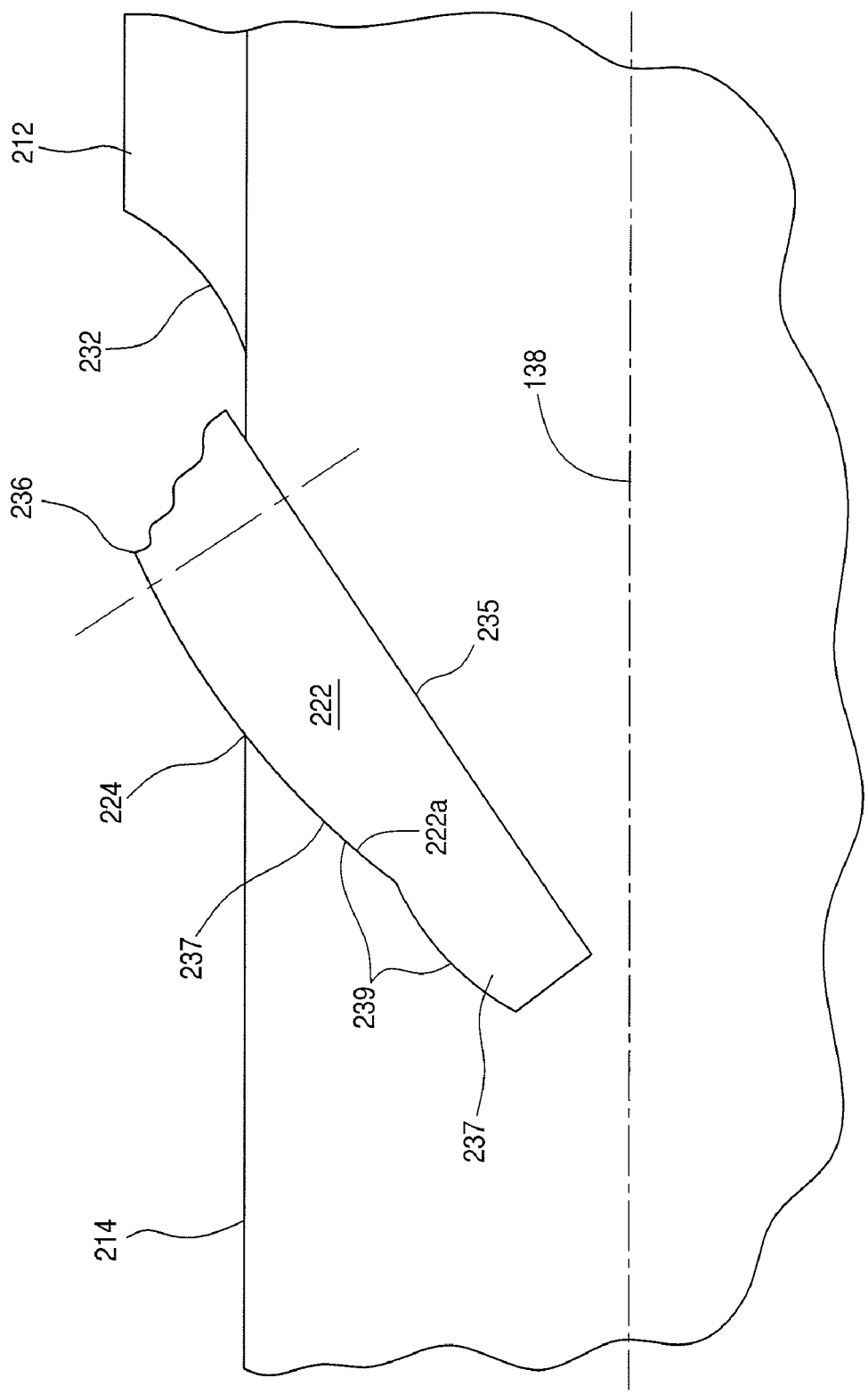
FIG. 18 is a cross sectional view in accordance with yet a further alternate embodiment.

Referring to FIGS. 17 and 18, the sharpness of the cutting edges 124, 132, 224, 232 may be increased by "hollow-grinding" the cutting edges 124, 132, 224, 232. This can be achieved on the inner cannula cutting edge 124, 224 by using a grinding wheel 136, 236 having opposed upper and lower grinding surfaces 135, 235, 137, 237, wherein the upper grinding surface(s) 137, 237 is convex to cut the recess 122, 222 and form a concave forward wall 122a, 222a (and in the case of the embodiment shown with reference to FIG. 18, having multiple convex surfaces 237 to produce multiple concave surfaces 239 along the forward wall 222a of the recess 222). The convex surface(s) 137, 237 on the grinding wheel 136, 236 will produce a concave, "hollow-ground" edge on the cutting edge 124, 224 of the inner cannula 114, 214. The same result can be achieved on the outer cannula 112, 212.

Due to the cutting rather than tearing operation, biopsy samples cut with the present biopsy needle should produce less trauma to the patient.

Figure 19:
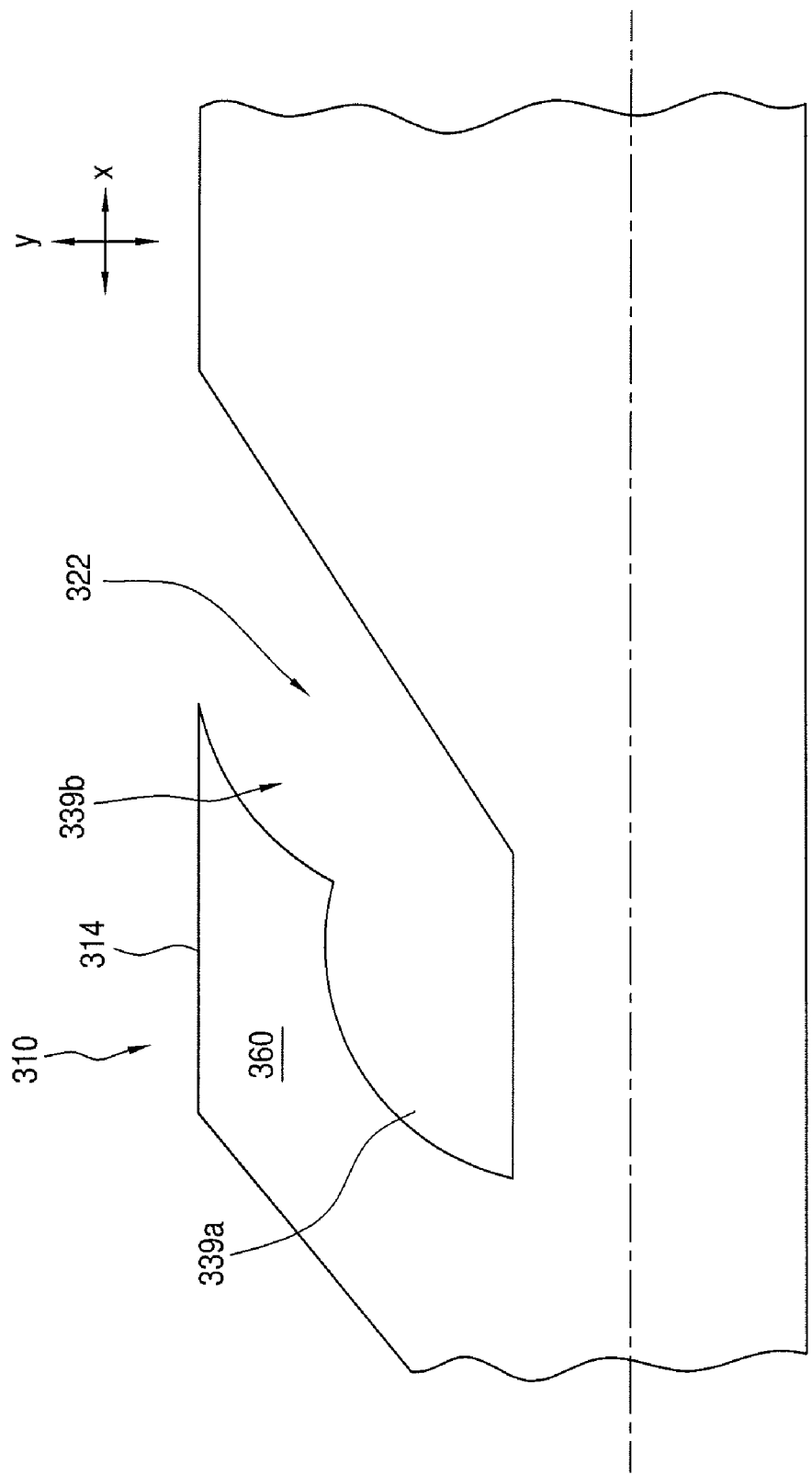
FIGS. 19, 20 and 21 respectively show a longitudinal cross-sectional view, a detailed longitudinal cross-sectional view and a lateral cross-sectional view in accordance with an alternate embodiment.
Figure 20:
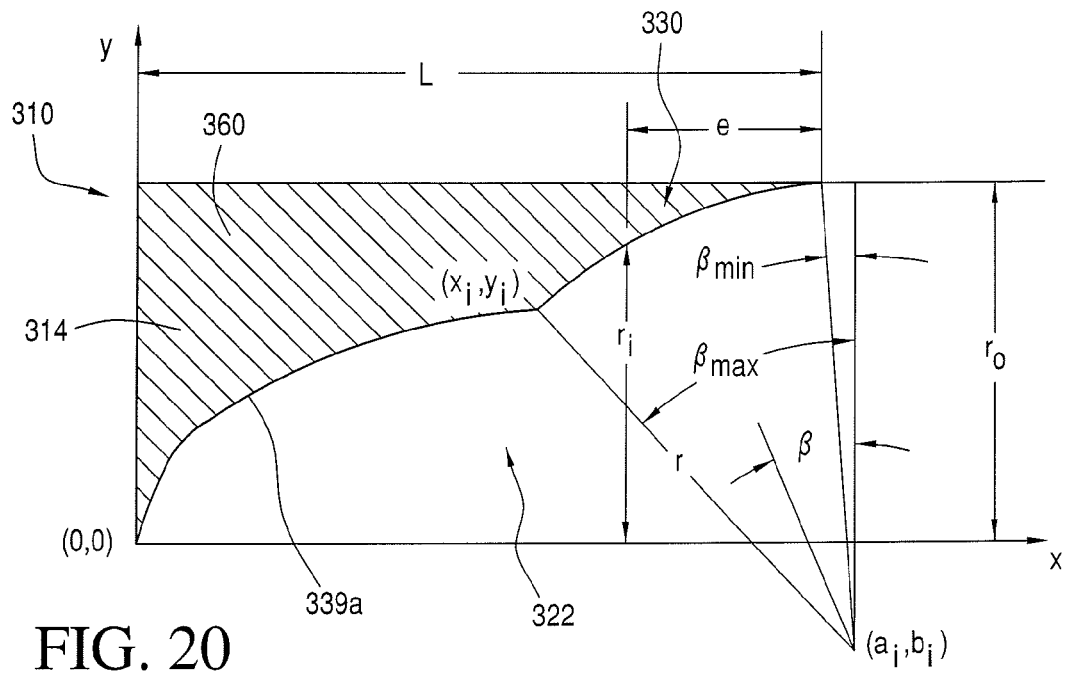
Figure 21:
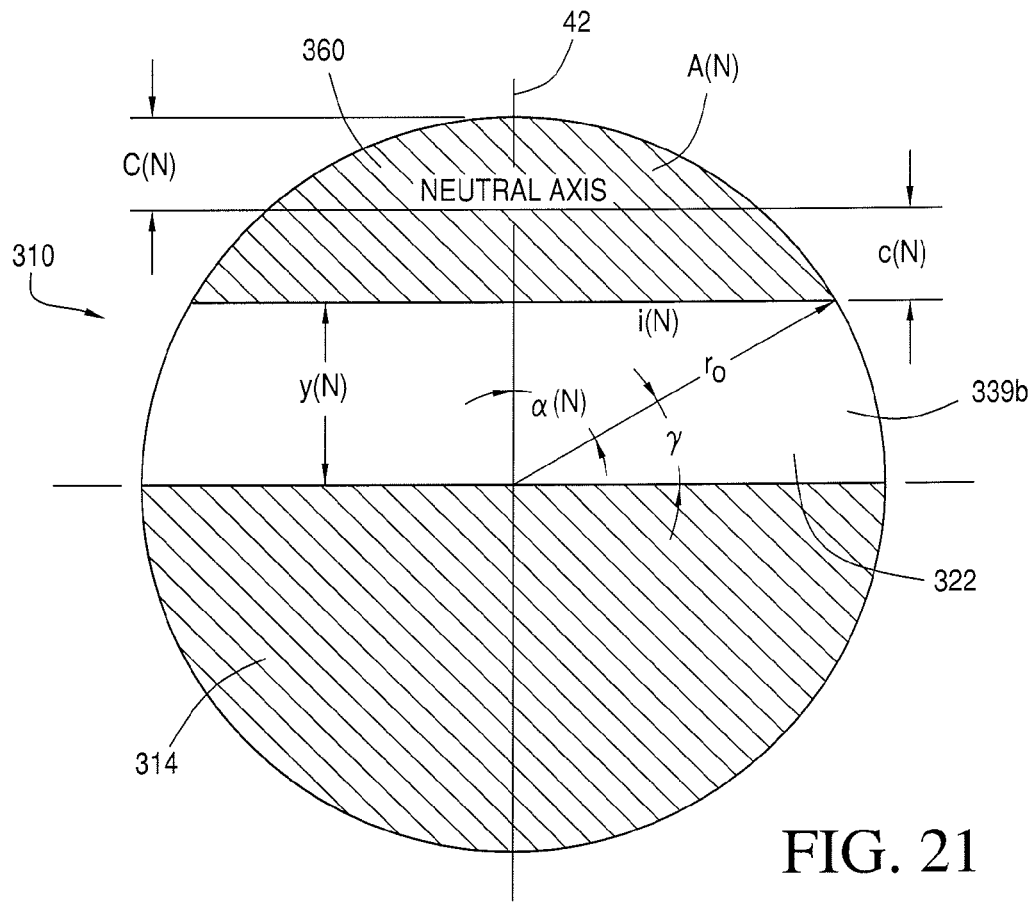

Further to the embodiment shown with reference to FIG. 18, an alternate embodiment with dual concave surfaces is disclosed in FIGS. 19, 20 and 21. More particularly, the design contains "multiple concave surfaces 239" forming a dual cavity biopsy supply recess 322 consisting of intersecting, parabolic and circular curves. The biopsy needle 310 in accordance with the embodiment provides a recess including dual intersecting cavities shaped and dimensioned to:

1) Provide sharp biopsy sample cutting edges;
2) Prevent undesirable bending of the sharp, biopsy cutting edges; and
3) Provide the desired volume of the biopsy sample The multiple cavity design employed in accordance with this embodiment may be represented in mathematical terms. All of the necessary equations for designing the parabolic/circular cavity are included herein. The mathematical approach to the design procedure as presented below includes all of the required equations and provides the numerical and graphical results.

Considering the design procedure for a biopsy needle 310 in accordance with a preferred embodiment having an inner cannula 314 with an intersecting, parabolic cavity 339a and circular cavity 339b, FIGS. 19 and 20 show the parabolic cavity 339a and circular cavity 339b. For orientation purposes, the needle point (not shown) is to the left of the cross sectioned portion in the negative x direction. The x-axis is in the axial direction of the biopsy needle 310. In the biopsy needle 310 presented herein in accordance with a preferred embodiment of the present invention, the x-axis is at the bottom of the biopsy sample recess 322. It may be along the center line of the biopsy needle 310 (or inner cannula 314) or above or below the centerline of the biopsy needle 310 (or inner cannula 314) depending on the design requirements.

The parabolic cavity 339a of the dual cavity design extends from the origin of the (x, y) coordinate system to the intersection of the parabolic cavity 339a and the circular cavity 339b at the point designated by xi, yi. The circular cavity 339b of the present dual cavity design extends from the point xi, yi to the end of the cavity length, L. The center of curvature for the circular cavity 339b of the dual cavity design is located at the point a1, b1. The axial length of any point on the circular cavity 339b of the dual cavity design is given by dimension, e. The length of the void portion of the circular cavity 339b at location, e, is designated, y1. The radius of the circular cavity 339b of the dual cavity design is designated, r. The angle to any point on the circular cavity 339b is designated, β. The minimum and maximum values of the angle, β, are designated β min and β max, respectively. The radius of the biopsy needle 310 is designed, ro.

FIG. 21 shows a transverse cross section through the inner cannula 314 of the biopsy needle 310 at location, y1. Note that, for this example, the bottom of the biopsy sample recess 322 is taken at the center line of the biopsy needle 310. The cross sectional area of the upper portion of the biopsy sample recess 322 is designated A(N). The neutral axis of the area A(N) is designated by C(N) and c(N). The generalized lengths of the dimensions i(N), y(N) and α(N) are shown in FIG. 21. The dimension i(N) is used to draw the view of the upper portion of the biopsy sample recess 322 as viewed along the y-axis and as shown in FIG. 20. Note that in the notation used above, i.e., A(N), C(N), c(N), etc., the upper-case N refers to the dimension in the circular cavity 339b of the dual cavity design. A lower-case n refers to the corresponding dimension in the parabolic cavity 339a of the dual cavity design.

The design procedure for the parabolic cavity 339a of the dual cavity design is disclosed below. The designer first selects the following parameters:

ro=radius of the inner cannula of the biopsy needle (inches)

xi=x coordinate of the parabolic/circular intersection (inches)

yi=y coordinate of the parabolic/circular intersection (inches)

a1=x coordinate of the center of curvature of the circular portion (inches)

b1=y coordinate of the center of curvature of the circular portion (inches)

r=the radius of the circular cavity

βmin=the minimum value of the angle β

βmax=the maximum value of the angle β

The following mathematical procedure is then implemented to calculate the radius of the circular cavity 339b, r, the minimum value of the angle, β, and the overall length of the biopsy sample recess 322, L.

$$ro := .0195 \quad xi := .024 \quad yi := .013 \quad a1 := .05 \quad b1 := -.03$$

$$k1 := \frac{xi}{ro}, \quad k2 := \frac{yi}{ro} \quad k3 := \frac{a1}{ro} \quad k4 := \frac{b1}{ro}$$

$$r := \sqrt{(a1 - xi)^2 + (yi - b1)^2}$$

$r = 0.050249$ radius of the circular portion $$\beta\min := a\cos\left(\frac{ro - b1}{r}\right) \cdot \frac{180}{\pi}$$

$\beta\min = 9.907498$ $$\beta\max := a\sin\left(\frac{a1 - xi}{r}\right) \cdot \frac{180}{\pi}$$

$\beta\max = 31.159305$ $$L := a1 - r \cdot \sin(\beta\min \cdot deg)$$

$L = 0.041354$ Total cavity length

It should be understood the values disclosed herein are merely exemplary and other values may be employed without departing from the spirit of the present invention. Substituting values of n into the equations for x(n), y(n), i(n) and α(n) determines the side and top views of the parabolic cavity 339a of the dual cavity design.

$$n := 0, .1 \ldots 1$$

$$x(n) := n \cdot xi$$

$$y(n) := yi \cdot \sqrt{n}$$

Where $0 < n < 1$ $$i(n) := \sqrt{ro^2 - y(n)^2}$$

$$\alpha(n) = a\sin\left(\frac{i(n)}{ro}\right) \cdot \frac{180}{\pi}$$

The properties of the upper portion of the biopsy sample recess 322 in the parabolic cavity 339a are then calculated using the equations for A(n), C(n), c(n) and I(n) (that is, the moment of inertia of the upper portion of the biopsy sample recess 322 in the parabolic cavity 339a).

A(n)=transverse area of the cantilever sector 360

C(n)=distance from the neutral axis (NA) to the extreme fiber above the NA c(n)=distance from the NA to the extreme fiber below the NA I(n)=moment of inertia of the area sector, A(n), about the NA $$A(n) := ro^2 \cdot \left(\frac{\alpha(n) \cdot \pi}{180} - \sin(\alpha(n) \cdot deg) \cdot \cos(\alpha(n) \cdot deg)\right)$$

$$C(n) := ro \cdot \left(1 - \frac{2 \cdot ro^2 \cdot \sin(\alpha(n) \cdot deg)^3}{3 \cdot A(n)}\right)$$

$$c(n) := ro \cdot \left(\frac{2 \cdot ro^2 \cdot \sin(\alpha(n) \cdot deg)^3}{3 \cdot A(n)} - \cos(\alpha(n) \cdot deg)\right)$$

$$I(n) := \frac{ro^4}{4} \cdot$$

$$\left(\frac{A(n)}{ro^2} + 2 \cdot \sin(\alpha(n) \cdot deg)^3 \cdot \cos(\alpha(n) \cdot deg) - \frac{16 \cdot ro^2 \cdot \sin(\alpha(n) \cdot deg)^6}{9 \cdot A(n)}\right)$$

The various parameters are then plotted for the parabolic cavity 339a as presented below and shown in FIG. 22.

$$x(n) = \begin{bmatrix} 0 \\ 2.4 \cdot 10^{-3} \\ 4.8 \cdot 10^{-3} \\ 7.2 \cdot 10^{-3} \\ 9.6 \cdot 10^{-3} \\ 0.012 \\ 0.0144 \\ 0.0168 \\ 0.0192 \\ 0.0216 \\ 0.024 \end{bmatrix} \quad y(n) = \begin{bmatrix} 0 \\ 4.110961 \cdot 10^{-3} \\ 5.813777 \cdot 10^{-3} \\ 7.120393 \cdot 10^{-3} \\ 8.221922 \cdot 10^{-3} \\ 9.192388 \cdot 10^{-3} \\ 0.01007 \\ 0.010877 \\ 0.011628 \\ 0.012333 \\ 0.013 \end{bmatrix} \quad i(n) = \begin{bmatrix} 0.0195 \\ 0.019062 \\ 0.018613 \\ 0.018154 \\ 0.017682 \\ 0.017197 \\ 0.016699 \\ 0.016185 \\ 0.015654 \\ 0.015105 \\ 0.014534 \end{bmatrix}$$

$$\alpha(n) = \begin{bmatrix} 90 \\ 77.829677 \\ 72.653935 \\ 68.583286 \\ 65.062017 \\ 61.874494 \\ 58.90907 \\ 56.09805 \\ 53.395724 \\ 50.76848 \\ 48.189685 \end{bmatrix} \quad A(n) = \begin{bmatrix} 5.972953 \cdot 10^{-4} \\ 4.381635 \cdot 10^{-4} \\ 3.739634 \cdot 10^{-4} \\ 3.259007 \cdot 10^{-4} \\ 2.864122 \cdot 10^{-4} \\ 2.525521 \cdot 10^{-4} \\ 2.228039 \cdot 10^{-4} \\ 1.962651 \cdot 10^{-4} \\ 1.723483 \cdot 10^{-4} \\ 1.506471 \cdot 10^{-4} \\ 1.308686 \cdot 10^{-4} \end{bmatrix}$$

$$C(n) = \begin{bmatrix} 0.011224 \\ 8.961949 \cdot 10^{-3} \\ 8.004164 \cdot 10^{-3} \\ 7.262141 \cdot 10^{-3} \\ 6.632184 \cdot 10^{-3} \\ 6.074056 \cdot 10^{-3} \\ 5.567087 \cdot 10^{-3} \\ 5.09898 \cdot 10^{-3} \\ 4.661709 \cdot 10^{-3} \\ 4.249693 \cdot 10^{-3} \\ 3.858864 \cdot 10^{-3} \end{bmatrix} \quad c(n) = \begin{bmatrix} 8.276057 \cdot 10^{-3} \\ 6.42709 \cdot 10^{-3} \\ 5.682059 \cdot 10^{-3} \\ 5.117466 \cdot 10^{-3} \\ 4.645894 \cdot 10^{-3} \\ 4.233555 \cdot 10^{-3} \\ 3.863156 \cdot 10^{-3} \\ 3.52444 \cdot 10^{-3} \\ 3.210738 \cdot 10^{-3} \\ 2.917424 \cdot 10^{-3} \\ 2.641136 \cdot 10^{-3} \end{bmatrix}$$

$$I(n) = \begin{bmatrix} 1.586977 \cdot 10^{-8} \\ 7.231062 \cdot 10^{-9} \\ 4.874213 \cdot 10^{-9} \\ 3.471196 \cdot 10^{-9} \\ 2.529149 \cdot 10^{-9} \\ 1.861032 \cdot 10^{-9} \\ 1.372968 \cdot 10^{-9} \\ 1.010472 \cdot 10^{-9} \\ 7.389225 \cdot 10^{-10} \\ 5.349217 \cdot 10^{-10} \\ 3.819313 \cdot 10^{-10} \end{bmatrix}$$

The procedure above is then repeated using the equations for the circular cavity 339b of the dual cavity design as follows:

$y1 := r \cdot \cos(\beta min \cdot deg) + b1$ $y1 = 0.0195$ Checks OK and $Bmax - \beta min = 21.251807$ Let $\beta(N) := N \cdot (\beta max - \beta min)$ Where $0 < n < 1$ $N := 0, .1 \ldots 1$ Let $\gamma(N) := \beta min + \beta(N)$ then $y1(N) := r \cdot \cos(\gamma(N) \cdot deg) + b1$ $i(N) := \sqrt{ro^2 - y1(N)^2}$ $e(N) := r \cdot \sin(\gamma(N) \cdot deg)$ $\zeta(N) := a\sin\left(\frac{i(N)}{ro}\right) \cdot \frac{180}{\pi}$ $$A(N) := ro^2 \cdot \left(\frac{\zeta(N) \cdot \pi}{180} - \sin(\zeta(N) \cdot deg) \cdot \cos(\zeta(N) \cdot deg)\right)$$

$$C(N) := ro \cdot \left(1 - \frac{2 \cdot ro^2 \cdot \sin(\zeta(N) \cdot deg)^3}{3 \cdot A(N)}\right)$$

$$c(N) := ro \cdot \left(\frac{2 \cdot ro^2 \cdot \sin(\zeta(N) \cdot deg)^3}{3 \cdot A(N)} - \cos(\zeta(N) \cdot deg)\right)$$

$$I(N) := \frac{ro^4}{4} \cdot$$

$$\left(\frac{A(N)}{ro^2} + 2 \cdot \sin(\zeta(N) \cdot deg)^3 \cdot \cos(\zeta(N) \cdot deg) - \frac{16 \cdot ro^2 \cdot \sin(\zeta(N) \cdot deg)^6}{9 \cdot A(N)}\right)$$

Figure 23:
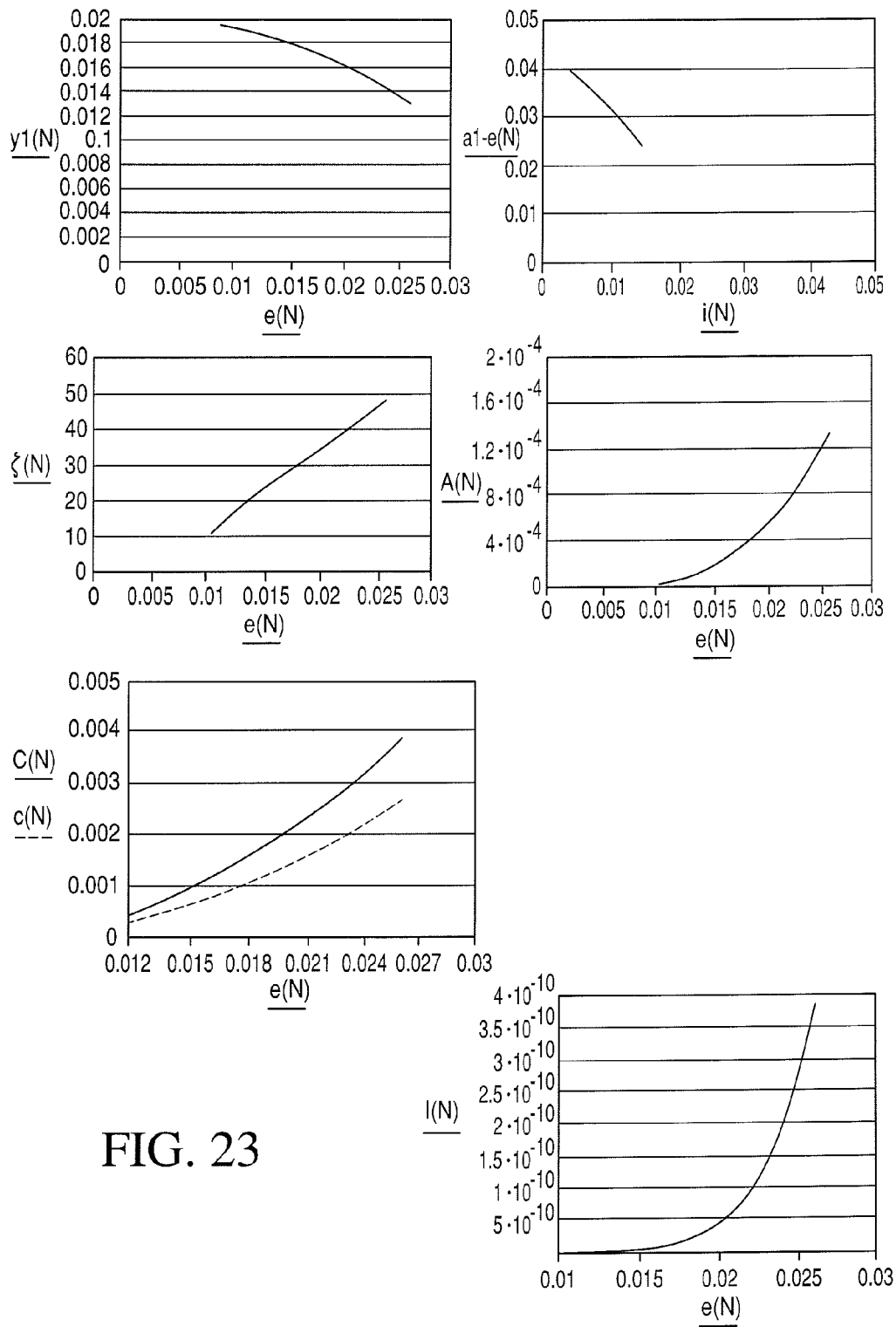

The results are presented below and plotted in FIG. 23.

$$N = \begin{bmatrix} 0 \\ 0.1 \\ 0.2 \\ 0.3 \\ 0.4 \\ 0.5 \\ 0.6 \\ 0.7 \\ 0.8 \\ 0.9 \\ 1 \end{bmatrix} \quad \gamma(N) = \begin{bmatrix} 9.907498 \\ 12.032679 \\ 14.157859 \\ 16.28304 \\ 18.408221 \\ 20.533401 \\ 22.658582 \\ 24.783763 \\ 26.908943 \\ 29.034124 \\ 31.159305 \end{bmatrix} \quad y1(N) = \begin{bmatrix} 0.0195 \\ 0.019145 \\ 0.018723 \\ 0.018234 \\ 0.017678 \\ 0.017057 \\ 0.016371 \\ 0.015621 \\ 0.014809 \\ 0.013935 \\ 0.013 \end{bmatrix}$$

$$i(N) = \begin{bmatrix} 3.292723i \cdot 10^{-10} \\ 3.702146 \cdot 10^{-3} \\ 5.449433 \cdot 10^{-3} \\ 6.912224 \cdot 10^{-3} \\ 8.23 \cdot 10^{-3} \\ 9.45046 \cdot 10^{-3} \\ 0.010594 \\ 0.011672 \\ 0.012687 \\ 0.013641 \\ 0.014534 \end{bmatrix} \quad a1 - e(N) = \begin{bmatrix} 0.041354 \\ 0.039525 \\ 0.037709 \\ 0.035911 \\ 0.034132 \\ 0.032375 \\ 0.030642 \\ 0.028936 \\ 0.027258 \\ 0.025612 \\ 0.024 \end{bmatrix}$$

-continued $$\zeta(N) = \begin{array}{|c|}\hline 9.674826i \cdot 10^{-7} \\\hline 10.944242 \\\hline 16.227865 \\\hline 20.761151 \\\hline 24.964161 \\\hline 28.988823 \\\hline 32.908743 \\\hline 36.76583 \\\hline 40.586762 \\\hline 44.390079 \\\hline 48.189685 \\\hline\end{array} \quad A(N) = \begin{array}{|c|}\hline 0 \\\hline 1.75387 \cdot 10^{-6} \\\hline 5.667921 \cdot 10^{-6} \\\hline 1.17477 \cdot 10^{-5} \\\hline 2.018631 \cdot 10^{-5} \\\hline 3.119182 \cdot 10^{-5} \\\hline 4.496202 \cdot 10^{-5} \\\hline 6.167523 \cdot 10^{-5} \\\hline 8.148523 \cdot 10^{-5} \\\hline 1.045179 \cdot 10^{-4} \\\hline 1.308686 \cdot 10^{-4} \\\hline\end{array}$$

$$C(N) = \begin{array}{|c|}\hline 5.833343 \cdot 10^{-4} \\\hline 2.126837 \cdot 10^{-4} \\\hline 4.656159 \cdot 10^{-4} \\\hline 7.582886 \cdot 10^{-4} \\\hline 1.090109 \cdot 10^{-3} \\\hline 1.460398 \cdot 10^{-3} \\\hline 1.86839 \cdot 10^{-3} \\\hline 2.313228 \cdot 10^{-3} \\\hline 2.793965 \cdot 10^{-3} \\\hline 3.309557 \cdot 10^{-3} \\\hline 3.858864 \cdot 10^{-3} \\\hline\end{array} \quad c(N) = \begin{array}{|c|}\hline -5.833343 \cdot 10^{-4} \\\hline 1.419744 \cdot 10^{-4} \\\hline 3.113053 \cdot 10^{-4} \\\hline 5.079198 \cdot 10^{-4} \\\hline 7.317377 \cdot 10^{-4} \\\hline 9.826735 \cdot 10^{-4} \\\hline 1.260639 \cdot 10^{-3} \\\hline 1.565547 \cdot 10^{-3} \\\hline 1.897313 \cdot 10^{-3} \\\hline 2.255863 \cdot 10^{-3} \\\hline 2.641136 \cdot 10^{-3} \\\hline\end{array}$$

$$I(N) = \begin{array}{|c|}\hline 0 \\\hline 1.513337 \cdot 10^{-14} \\\hline 2.348039 \cdot 10^{-13} \\\hline 1.2934 \cdot 10^{-12} \\\hline 4.603885 \cdot 10^{-12} \\\hline 1.280157 \cdot 10^{-11} \\\hline 3.029371 \cdot 10^{-11} \\\hline 6.390792 \cdot 10^{-11} \\\hline 1.236267 \cdot 10^{-10} \\\hline 2.233887 \cdot 10^{-10} \\\hline 3.819313 \cdot 10^{-10} \\\hline\end{array}$$

Figure 26:
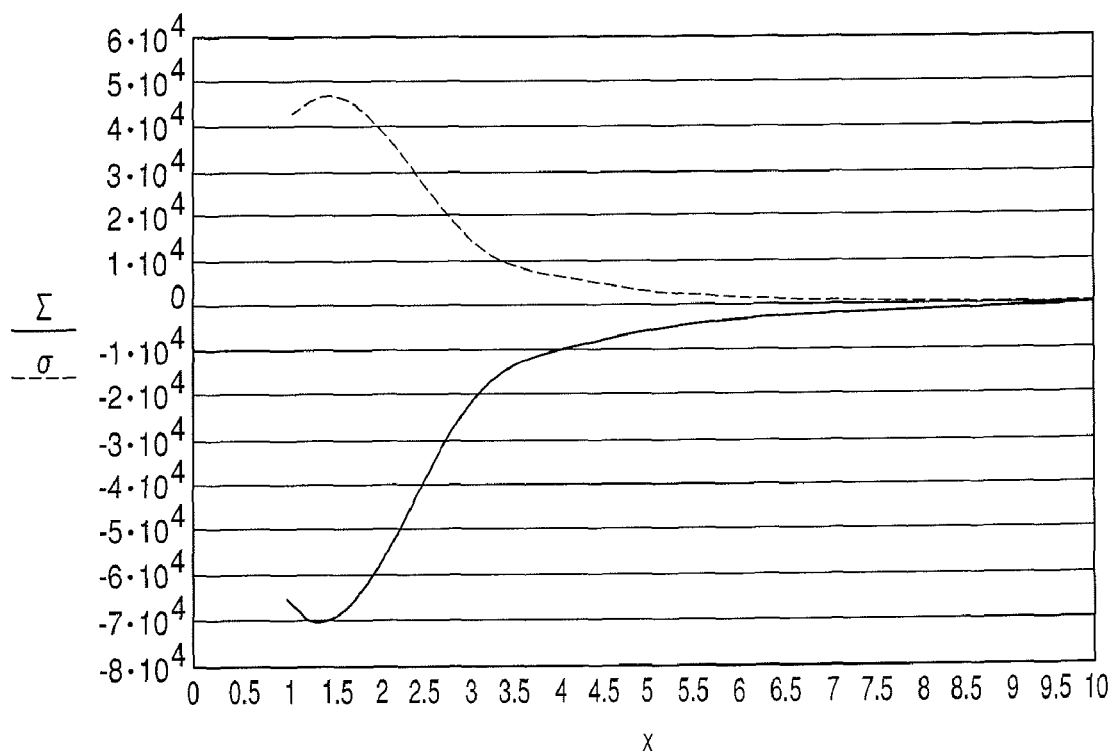

The values for x, y and i in FIG. 24 are then plotted so that the side and top views, FIG. 25, of the entire biopsy sample recess 322 may be evaluated based on the design requirements. Using conventional engineering techniques, an approximate study of the fiber stresses developed at the centerlines of the upper and lower surface of the upper portion of the biopsy sample recess 322 may be undertaken (that is, along the centerline of the parabolic cavity 339b, the centerline of the circular cavity 339b, and the centerline of the outer diameter of the inner cannula 314 of the biopsy needle 310 located above the centerlines 339a and 339b). The approximate stress values for the design herein are given in FIG. 26.

Based on the results obtained for this design, the designer may then decide to lower the stress, for example, by modifying the circular cavity 339b. Shortening and/or thickening of the circular cavity 339b will lower the stresses and deformation of the circular cavity 339b of the biopsy sample recess 322. This may be achieved by changing the coordinates of the intersection xi, yi. For example, using a larger value for xi and/or a smaller value for yi, will lower the stresses and deformation in the tip of the circular cavity 339b of the biopsy sample recess 322

Similarly, the volume of the biopsy sample recess 322 may be increased by modifying the values of xi, yi or possibly changing from a parabolic profile of the parabolic cavity 339a to an elliptical profile, etc.

The example herein considers only two mathematical curves to generate the biopsy sample recess. The biopsy sample recess may also be generated by using more than two mathematical curves or a multiplicity of straight line segments.

Figure 27:
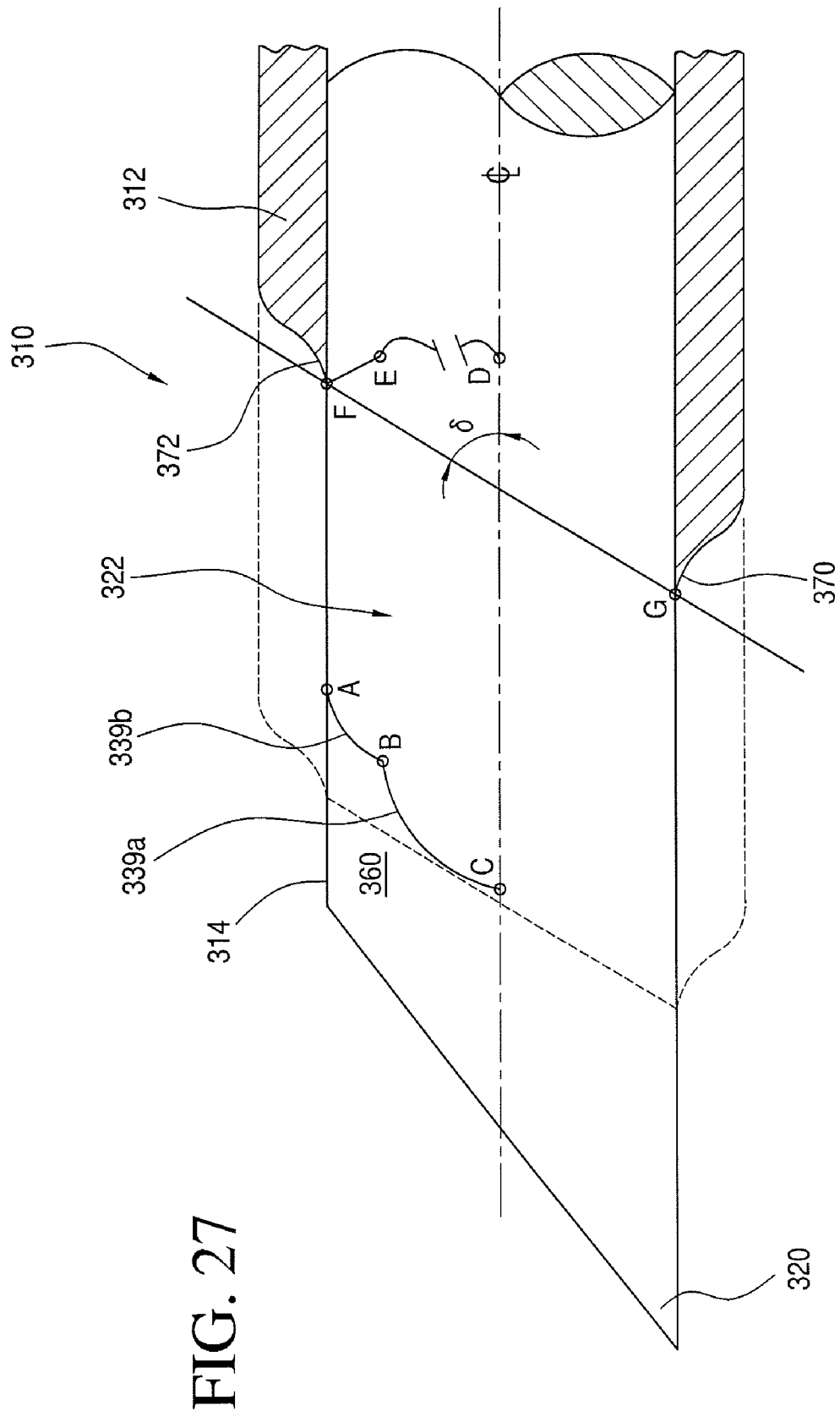

FIG. 27 shows the assembled biopsy needle 310 with the inner cannula 314 and the surrounding outer cannula 312. The outer cannula 312 is shown with hollow ground, biopsy sample cutting edges 370, 372. These, of course, may also be beveled edges, etc. The cannula bevel angle, δ, is selected so that the biopsy sample recess 322 (as defined by the points labeled A, B, C, D, E, F) is completely open before the biopsy sample is taken and completely closed by the outer cannula 312 after the biopsy sample is taken. The D, E, F portion of the biopsy sample recess 322 may or may not be a mirror image of the portion C, B, A. In any event, the portion E, F should make an acute angle with the top of the inner cannula 314 of the biopsy needle 310 as shown in FIG. 27.

When the outer cannula 312 is in the cross-hatched position, the biopsy sample recess 322 is open. When the outer cannula 312 is in the dotted position, the biopsy sample recess 322 is closed and the biopsy sample is contained within the biopsy sample recess 322.

Various known mechanisms may be used to move the outer cannula 312 relative to the inner cannula 314 of the needle 310. For example, the inner cannula 314 and the outer cannula 312 may be spring loaded to move in opposite directions. Alternatively, one may remain fixed while the other moves to cut off the required biopsy sample.

In use, the biopsy sample recess 322 is opened after the biopsy needle 310 is inserted to the desired location. The biopsy sample is then excised by moving the inner cannula 314 and outer cannula 312 as described above.

The design procedure presented above enables the biopsy needle designer to produce a biopsy sample recess 322 having a sharp cutting edge such as indicated by point A, in portion AB (see FIG. 27). Further, it enables the designer to produce a cutting edge, A, which will not undergo permanent deformation during excision of the biopsy sample. Further, portion BC may be designed to maximize the size of the biopsy sample by having the inner cannula 314 of the biopsy needle 310 begin its movement toward the outer cannula 312 before the outer cannula 312 starts to move toward the tip 320 of the needle 310 (that is, the tip of the inner cannula 312).

In addition, the bevel angle, δ enables the outer cannula 312 to stiffen the inner cannula 314 (and ultimately the biopsy needle 310) in the region of the biopsy sample. The stiffening is effected by positioning the biopsy sample recess 322 and the long end, G of the outer cannula 312 180 degrees apart. Excision of the biopsy sample imparts a bending load on the tip of the biopsy sample recess 322 at point C. However, movement of the outer cannula 312 toward the tip 320 of the biopsy needle 310 during sample excision effectively shortens the length of the biopsy sample recess 322 thereby reducing the bending load. Since the transverse deflection of the biopsy sample recess 322 is a cubic function of the length of the sample recess CD, siqnificant stiffening of the tip 320 of the biopsy needle 310 is obtained during sample excision. As a result of the stiffening, the bottom of the sample recess CD may be located below the center line of the biopsy needle 310 which will result in the excision of a larger sample which is often a beneficial result.

The examples presented herein only cover biopsy needle cavities having two different geometric profiles, namely, parabolic and circular. It is, however contemplated the biopsy sample recess may be composed of other geometric configurations so long as the biopsy sample recess is as sharp as possible without undergoing permanent deformation or fracture of the cutting edge during acquisition of the biopsy sample. With this in mind, and with reference to FIGS. 28-36, a "radial step" 480 is incorporated into the biopsy sample recess 422. The equations and procedures necessary to achieve sharp cutting edges 424 while maintaining sufficient strength of the cutting edge 424 so that the cutting edge 424 is not damaged during acquisition of the sample are described below.

Figure 28:
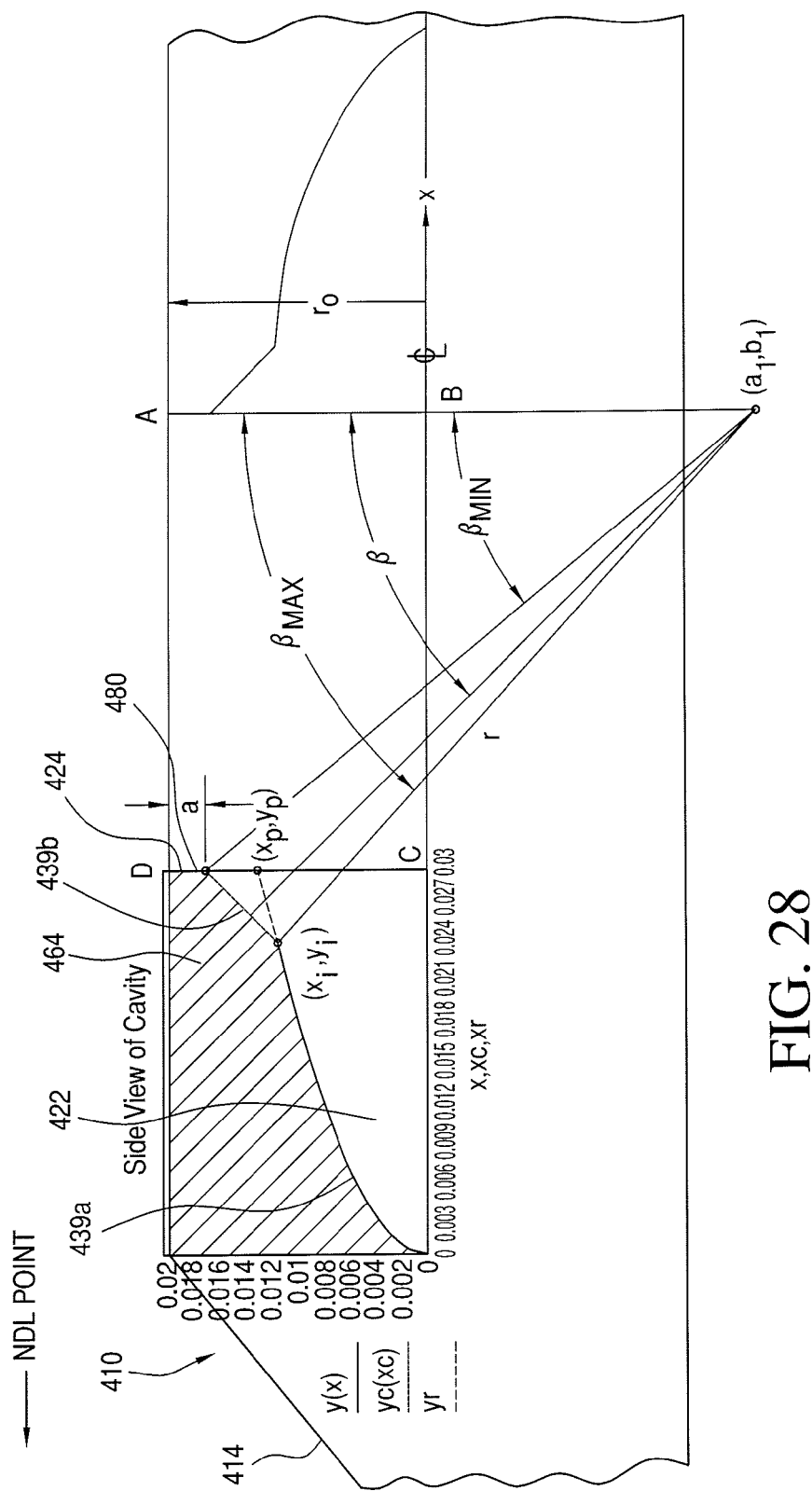
FIG. 28 is a cross section view in accordance with another alternate embodiment of the present.

The following procedure describes the benefits and use of "radial steps" 480 in the design of a biopsy sample recess 422 that have a sharp cutting edges 424 such that the cutting edge 424 will not fail by permanent deformation or fracture. Further to the embodiment shown with reference to FIGS. 17 thru 21, an alternate embodiment using a 0.003" radial step 480 is shown in FIG. 28. This embodiment uses a parabolic/circular dual cavity 439a, 439b as in the earlier embodiment. However, and in accordance with the embodiment disclosed herein, a 0.003" radial step 480 is incorporated into the free end 464 of the cantilevered, parabolic/circular sample recess 422 to lower the fiber stress at the free end 482 of the cantilever 460 defined by the biopsy sample recess 422. The cantilever 460 is considered to be that position of the inner cannula 414 that is distal to the biopsy sample recess 422. As such, the biopsy sample recess 422 is the fulcrum about which the distal portion, that is, the cantilever 460 rotates when lateral pressure is applied thereto. Excessive fiber stress levels at the free end 464 of the cantilever 460 may result in permanent deformation at the tip 462 of the cantilever 460 which will prevent complete severance of the biopsy sample and complete closure of the biopsy sample recess 422. The 0.003" radial step 480 completely removes the very thin portion of the free end 464 of the cantilever 460 which is highly susceptible to permanent deformation.

The portion of the cantilevered 460 adjacent to the 0.003" radial step 480 in the embodiment disclosed with reference to FIG. 28 is circular. The center of curvature of the circular portion is selected so that the depth of the section at the free end 464 of the cantilever 460 increases rapidly thereby maintaining the fiber stresses at acceptable levels at the free end 464 of the cantilever 460 with a negligible reduction in sharpness.

The parabolic portion 439a of the biopsy sample recess 422 intersects the circular portion 439b of the biopsy sample recess 422 at location (xi,yi). The parabolic portion 439a serves to provide a relatively large volume at the distal end of the biopsy sample recess 422 while maintaining acceptable fiber stress levels and support for the circular portion 439b of the biopsy sample recess 422. Hence, the dual cavity design provides the sharpness required to sever and hold the biopsy sample so that it may be excised with minimal trauma for the patient.

With regard to the section of the needle 410 proximal to the dual cavity 439a, 439b, it may be formed as a mirror image of the distal portion of the sample recess 422 or it may be simply as per cavity ABC. In addition, it should be noted that length AD may be selected by the designer of the needle depending upon specific needs.

It should be noted that although the dual cavity in this embodiment was selected as parabolic and circular, it is not limited to this geometry. The sub portions of the biopsy sample recess may have conventional geometries such as parabolic, elliptical, linear etc. Further, the number of sub portions in this embodiment was two. Namely, parabolic and circular. Any number of sub portions may be used to achieve the desired sharpness and biopsy sample holding capability using the concept and equations provided. The designer may select any geometry combination, any number of sub cavity portions, and any radial step depth to meet the design requirements.

As an example of the use of the design procedure, consider the geometry shown in FIG. 28. This embodiment has a parabolic/circular dual cavity and a 0.003" radial step 480 at the free end 464 of the cantilever 460. Consider first the following definition of terms used in the equations:

ro=outer radius of the solid, cylindrical portion of the inner cannula of the biopsy needle;
r=radius used to form the radial step;
a=length of the radial step;
KN=geometry ratios where 0<N<1;
(a1,b1)=(x,y) location of the center of curvature of radius, r;
(xp,yp)=(x,y) location of the end of the parabolic sub portion of the dual cavity;
(xi,yi)=(x,y) location of the intersection of the parabolic and circular sub portions of the biopsy sample recess;
βmax & βmm=angles defined on FIG. 28;
Equations β(N) through ζ(N) are defined in FIG. 30;
Equations A(N) through I(N) are section properties of the circular segments of the circular portion of the dual cavity, where:
A(N)=normal area of circular portion N;
C(N)=radial distance from the neutral axis (NA) of the circular segment N to the extreme fiber above the NA;
c(N)=radial distance from the NA of the circular segment N to the extreme fiber below the NA;
I(N)=moment of inertia of area segment A(N) about the NA;
S(N)=minimum fiber stress above the NA in circular segment N; and
s(N) maximum fiber stress below the NA in circular segment N.

An design procedure is disclosed in accordance with the present invention with reference to FIGS. 29 to 36 and as follows:

As shown in FIG. 29, the designer begins by selecting values of the parameters a1, b1, xp, yp and a
The KN ratios for N=1 through N=5 are then calculated as per FIG. 29.
Based on the data above, the radius of the circular portion of the cavity, r, is calculated as per FIG. 29 using (a1,b1) as the center of curvature and "a" as the depth of the radial step. For this embodiment, ro=0.0195", xp=0.03", a1=0.062", b1=−0.0225", a=0.003" from which we obtain r=0.050".

The equations for the parabolic and circular portions of the dual cavity biopsy sample recess are given in terms of their KN values in FIG. 29.

The intersection of the parabolic and circular portions of the dual cavity biopsy sample recess, (xi,yi), can be readily calculated by hand or using a computer program such as MATHCAD.

The equations necessary for completing the design are given in FIG. 30.

The numerical and graphical results are given in FIGS. 31 through 33A.

Figure 35:
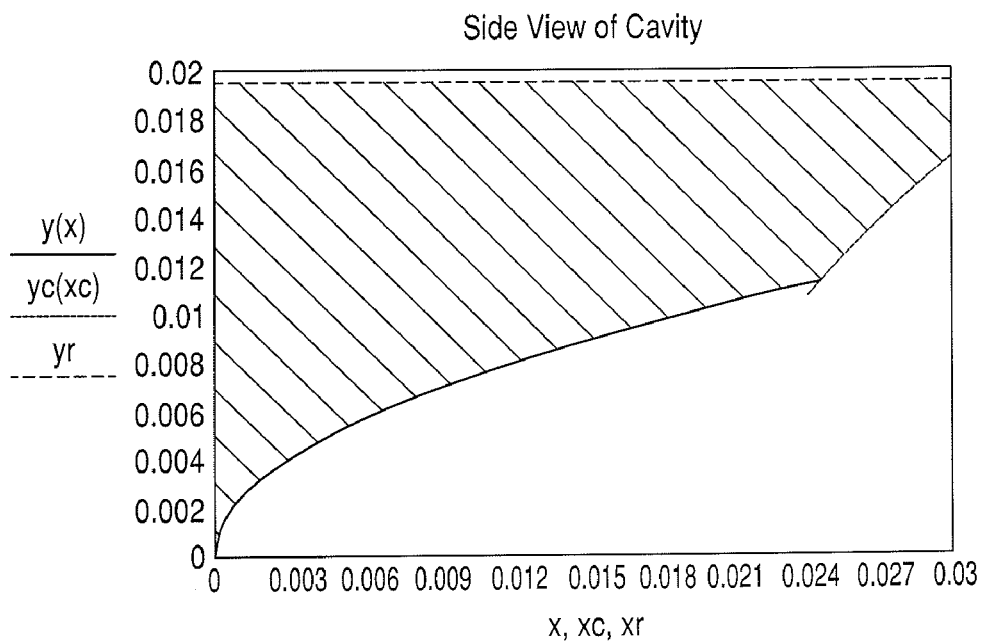
Figure 36:
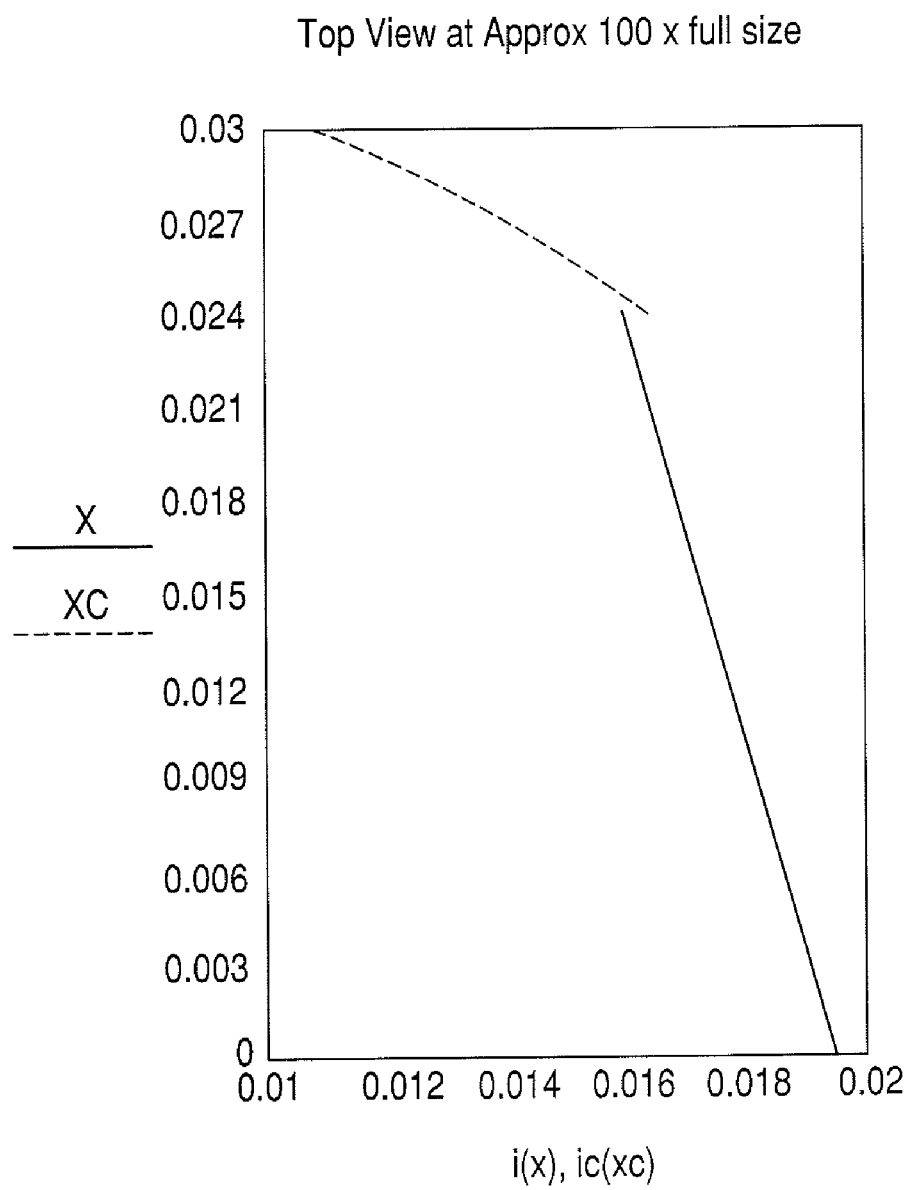

The procedure for obtaining the side and top views of the dual cavity biopsy sample recess is given in FIGS. 34 through 36.

The side and top views shown in FIGS. 35 and 36 are approximately 100 times full size. The free end of the cantilever is a circular sector which has a total width of 0.0208" and a radial height which varies from zero at the ends of the sector, that is, sharp edges, to a maximum dimension of 0.003" at the center of the sector. The normal, that is, perpendicular, area of the free end of the cantilever is given in FIG. 31 as $A(0)=42\times10^{-6}$ square inches which should not result in a detectable reduction in sharpness, needle insertion force or trauma to the patient.

Past experience with medical devices such as hypodermic needles clearly demonstrates the high susceptibility of hypodermic needles, or for that matter, any sharp, pointed, metallic object, to point damage. The reduction in area as the point is approached increases very rapidly and the yield point of the material is easily exceeded resulting in permanent deformation or fracture of the point at very low force values. A radial step, in this embodiment, the 0.003" radial step, reduces the magnitude of the fiber stresses at the tip of the cantilever by several orders of magnitude thereby preventing tip damage during excision of the biopsy sample.

It should be noted that, since the nature of the actual load distribution on the cantilevered portion of the biopsy needle is unknown and variable as the biopsy is underway, the loading in the embodiments included herein were assumed to be of a severe nature. The loadings were assumed to be 1 pound concentrated end loads at the end of the cantilever. The orders of magnitude of stress reduction obtained by using the radial step should certainly offset the uncertainty in the nature of the load distribution.

The design results for the embodiment shown herein are given numerically and graphically in FIGS. 28 through 36. Values of the parameter "N" range from zero to one where the value N=0 refers to the 0.003" radial step location along the x axis and the value N=1 refers to the point of intersection of the parabolic and circular portions of the dual cavity biopsy sample recess along the x axis. Thus, the entire range of the parameter N covers only the circular portion of the dual cavity biopsy sample recess where the fiber stresses will be highest.

Figure 33:
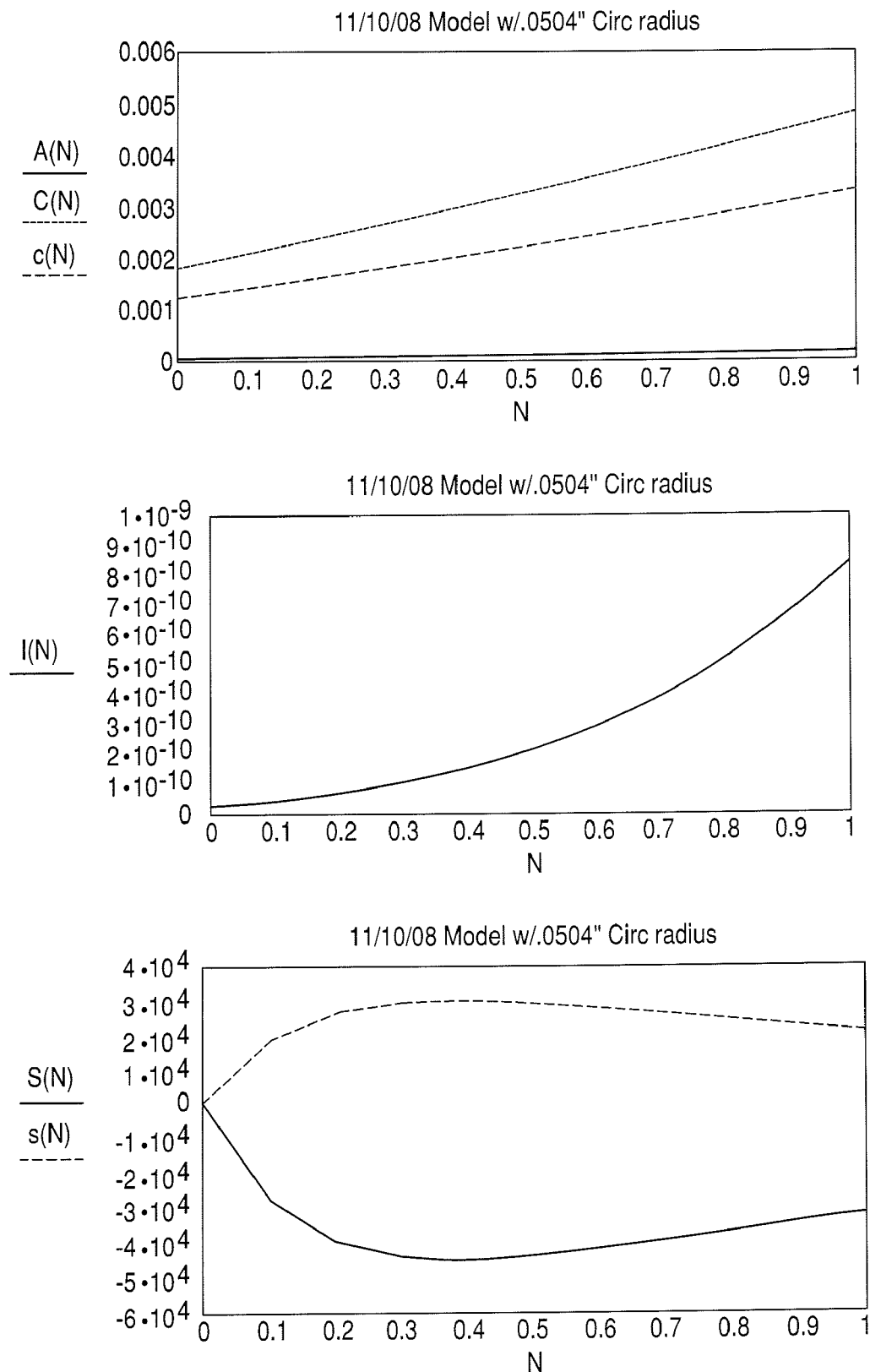

Using conventional engineering practice, the fiber stresses at location N=0 are zero because the length of the bending moment arm is zero at this location. The fiber stresses in FIG. 33 are compressive in the region above the neutral axis (NA) and tensile in the region below the NA of the circular sector. The maximum values of the stress magnitudes occurs at about N(0.35). The axial distance of this location from the 0.003" step is 0.002". FIG. 33A shows maximum magnitudes for these stresses as −44,265, that is, compressive, and 30,064, that is, tensile psi/# end load. For comparison purposes, FIG. 33A shows stress values of −33,156 and 21,491 psi/# end load at the intersection of the parabolic and circular portions of the dual cavity biopsy sample recess.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A biopsy needle, comprising:
   an outer cannula;
   an inner cannula including a distal end and a proximal end, the outer cannula being shaped and dimensioned to closely circumscribe the inner cannula for movement relative thereto;
   the inner cannula further including a sample recess at the distal end of the inner cannula, the sample recess including a forward wall and a rearward wall, the forward wall including multiple concave surfaces composed of a first cavity intersecting with a second cavity wherein the first cavity has a first shape and the second cavity has a second shape;
   wherein the first shape is different from the second shape, the first cavity having a parabolic shape and the second cavity having a circular shape.

\* \* \* \* \*